United States Patent
Ophardt

(10) Patent No.: US 11,172,791 B2
(45) Date of Patent: *Nov. 16, 2021

(54) DISPENSER WITH CONTAMINANT SENSOR

(71) Applicant: OP-Hygiene IP GmbH, Niederbipp (CH)

(72) Inventor: Heiner Ophardt, Arisdorf (CH)

(73) Assignee: OP-Hygiene IP GmbH, Niederbipp (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/690,785

(22) Filed: Nov. 21, 2019

(65) Prior Publication Data

US 2020/0100627 A1 Apr. 2, 2020

Related U.S. Application Data

(63) Continuation of application No. 15/204,891, filed on Jul. 7, 2016, now Pat. No. 10,524,621, which is a (Continued)

(30) Foreign Application Priority Data

| Nov. 4, 2011 | (CA) | 2757195 |
| Dec. 22, 2011 | (CA) | 2762731 |
| May 29, 2012 | (CA) | 2778470 |

(51) Int. Cl.
*A47K 10/32* (2006.01)
*A47K 5/12* (2006.01)
(Continued)

(52) U.S. Cl.
CPC ............ *A47K 5/1217* (2013.01); *A47K 5/12* (2013.01); *A47K 5/1202* (2013.01); *A47K 5/1211* (2013.01); *A47K 10/32* (2013.01); *A47K 13/26* (2013.01); *C12Q 1/04* (2013.01); *G08B 21/182* (2013.01); *G08C 17/02* (2013.01); *A47K 5/1205* (2013.01); *A47K 2010/3226* (2013.01); *G08B 21/12* (2013.01)

(58) Field of Classification Search
CPC ......... A47K 10/32; A47K 13/26; A47K 5/12; A47K 5/1202; A47K 5/1211; A47K 2010/3226; A47K 5/1205; C12Q 1/04; G08B 21/182; G08B 21/12; G08C 17/02
See application file for complete search history.

(56) References Cited

U.S. PATENT DOCUMENTS

| 3,864,676 A | 2/1975 | Macias |
| 6,206,238 B1 | 3/2001 | Ophardt |

(Continued)

FOREIGN PATENT DOCUMENTS

| JP | 11272946 | 10/1999 |
| WO | 2004096694 | 11/2004 |

OTHER PUBLICATIONS

US 8,773,596 B2, 05/2014, Ophardt et al. (withdrawn)

*Primary Examiner* — Hai Phan
*Assistant Examiner* — Anthony D Afrifa-Kyei
(74) *Attorney, Agent, or Firm* — Thorpe North & Western, LLP

(57) ABSTRACT

A fluid dispenser including a contaminant sensor and methods of use of such a fluid dispenser to monitor contaminants either alone or in an array of similar dispensers within a facility.

24 Claims, 31 Drawing Sheets

Related U.S. Application Data continuation of application No. 14/355,487, filed as application No. PCT/CA2012/001014 on Nov. 1, 2012, now Pat. No. 9,437,103.

(51) Int. Cl.

| | | |
|---|---|---|
| *C12Q 1/04* | (2006.01) | |
| *G08C 17/02* | (2006.01) | |
| *A47K 13/26* | (2006.01) | |
| *G08B 21/18* | (2006.01) | |
| *G08B 21/12* | (2006.01) | |

(56) References Cited

U.S. PATENT DOCUMENTS

| | | | |
|---|---|---|---|
| 7,053,524 B2 | 5/2006 | Edmonson | |
| 7,247,140 B2 | 7/2007 | Ophardt | |
| 7,287,929 B1 | 10/2007 | Sokolowski | |
| 7,451,894 B2 | 11/2008 | Ophardt | |
| 7,455,197 B2 | 11/2008 | Ophardt | |
| 7,530,477 B2 | 5/2009 | Ophardt | |
| 7,651,843 B2 | 1/2010 | Stubbs | |
| 7,748,573 B2 | 7/2010 | Anhuf et al. | |
| 7,875,173 B1 | 1/2011 | Barnes | |
| 7,980,421 B2 | 7/2011 | Ophardt et al. | |
| 8,245,877 B2 | 8/2012 | Ophardt | |
| 8,622,243 B2 | 1/2014 | Ophardt et al. | |
| 8,684,236 B2 | 4/2014 | Ophardt | |
| D780,473 S | 3/2017 | Brownley et al. | |
| 9,756,989 B2 | 9/2017 | Ophardt et al. | |
| 2004/0026449 A1* | 2/2004 | Goodman | B67D 1/16 222/108 |
| 2005/0029301 A1 | 2/2005 | Kyle | |
| 2005/0247735 A1 | 11/2005 | Muderlak | |
| 2006/0107753 A1 | 5/2006 | Mett | |
| 2006/0207753 A1 | 9/2006 | Sanatgar | |
| 2008/0145890 A1 | 6/2008 | Stubbs et al. | |
| 2009/0140004 A1* | 6/2009 | Scorgie | A47K 5/1217 222/52 |
| 2010/0140499 A1 | 6/2010 | Casale | |
| 2010/0328076 A1 | 12/2010 | Kyle | |
| 2012/0158419 A1* | 6/2012 | Nuthi | G08B 21/245 705/2 |
| 2014/0285344 A1* | 9/2014 | Best | G08B 21/245 340/573.1 |

\* cited by examiner

DISPENSER WITH CONTAMINANT SENSOR

RELATED APPLICATION

This application is a continuation application of co-pending U.S. patent application Ser. No. 15/204,891 filed Jul. 7, 2016 which is a continuation of co-pending U.S. patent application Ser. No. 14/355,487 filed Nov. 1, 2012 which issued to U.S. Pat. No. 9,437,103 on Sep. 6, 2016 and which claims the benefit of 35 U.S.C. 120.

SCOPE OF THE INVENTION

This invention relates to a contaminant sensing dispenser and, more particularly, to a dispenser to dispense product to a user which incorporates a contaminant sensor and provide indications of contaminant presence at a single dispenser and in an array of such dispensers within a facility. The invention more particularly relates to such a contaminant sensing dispenser, an array of such dispensers and methods of use of the dispenser and arrays of such dispensers.

BACKGROUND OF THE INVENTION

Fluid dispensers are known for dispensing cleaning and disinfecting fluids as liquids and foam for cleaning of a user's hands. Such dispensers are provided in many facilities such as in hospitals, health care premises, restaurants, food processing areas, office buildings, schools, airports and the like. Paper towel dispensers are known for dispensing paper towels as to persons in a washroom.

The growth and presence of contaminants in many facilities has become increasingly problematic. For example, the growth and presence of pathogens such as bacteria and viruses in hospitals has become a significant problem. Present methods of detection of such contaminants have disadvantages that they are not adequate and notably do not provide advance warnings of dangerous levels of contaminants. Present detection systems typically are so disadvantaged that warning of dangerous contaminant situations arises after patients have been negatively affected and exhibit symptoms of the pathogens.

SUMMARY OF THE INVENTION

To at least partially overcome these disadvantages of previously known devices, the present invention provides a dispenser including a contaminant sensor and methods of use of such a dispenser to sense contaminants either alone or in an array of similar dispensers within a facility.

An object of the present invention is to provide an improved dispenser, preferably for dispensing product, particularly a dispenser for dispensing hand cleaning fluid or paper towels incorporating a contaminant sensor.

Another object of the present invention is to provide an array of dispensers each including a sensor with the dispensers in the array disposed at spaced locations within a facility to monitor contaminants within the facility.

Another object is to provide a method of operating a dispensing sensor alone or in an array of similar dispensers to advantageously monitor for a contaminant.

In one aspect, the present invention provides a method of monitoring a contaminant and or a physical property in a facility comprising:

providing a dispenser for dispensing personal products to a user, the dispenser carrying a sensor capable of detecting the presence and relative level of the contaminant on the sensor or a physical property about the sensor, generating, for the dispenser periodically over time, signals representative of the level of the contaminant on the sensor or the level of the physical property about the sensor or the level of the physical property about the sensor at different times, optionally converting the signals to data representative of the level of the contaminant on the sensor or the level of the physical property about the sensor at different times, and optionally comparing the level sensed with one or more thresholds and determining if the level meets the thresholds, wherein the dispenser is preferably selected from a paper towel dispenser and a fluid dispenser for dispensing fluid including a liquid containing reservoir and a pump to dispenser fluid from the reservoir and the sensor is preferably provided on an external surface of the dispenser open to the environment bout the dispenser.

In another aspect, the present invention provides a method of monitoring a contaminant in a facility comprising:

providing a plurality fluid dispensers at spaced locations about a facility including a plurality of fluid dispensers for dispensing fluid for cleaning persons hands, each dispenser comprising a liquid containing reservoir and a pump to dispense fluid from the reservoir, each dispenser carrying a sensor capable of detecting the presence and relative level of the contaminant, generating, for each dispenser periodically over time, signals representative of the level of the contaminant on each sensor at different times, optionally converting the signals to data representative of the level of the contaminant on each sensor at different times, and optionally comparing the level of the contaminant sensed with one or more thresholds and determining if the level of contaminant does not meet the thresholds.

In yet another aspect, the present invention provides a contaminant sensing system for a facility comprising:

a common processor, a plurality of fluid dispensers located at spaced locations within the facility, each said dispenser comprising a replaceable liquid containing reservoir and a pump to dispense fluid from the reservoir, each reservoir including a sensor, the sensor sensing the presence of biologic contaminants, the biologic contaminants selected from bacteria, viruses and other pathogens, the sensor generating a signal when a contaminant is sensed, each dispenser including a communications system for communicating the signal to a common processor, and the common processor monitoring the level of biologic contaminants on each dispenser periodically over time.

In yet another aspect, the present invention provides a fluid dispenser for dispensing fluid for cleaning person's hands, the dispenser comprising a liquid containing reservoir and a pump to dispense fluid from the reservoir, the dispenser carrying a sensor on the surface capable of detecting the presence and relative level of the contaminant, a signal generator for generating a signal representative of the level of the contaminant on the sensor, and a processor for converting the signal to data representative of the level of the contaminant on the sensor at different times and for comparing the level of the contaminant sensed with one or more thresholds and providing a warning signal when the level of contaminant exceeds the thresholds wherein preferably the dispenser includes an external surface open to the environment about the dispenser and the sensor is provided to sense contaminants from the environment.

In a further aspect, the present invention provides a method of operating a fluid dispenser for dispensing fluid for cleaning a person's hands comprising:

discharging as discharged fluid, a hand cleaning fluid, from a discharge outlet, capturing a portion of the discharged fluid in a drip tray disposed below the discharge outlet, passing the portion of the discharged fluid to a sensor, and detecting with the sensor a relative level of a contaminant.

In yet a further aspect, the present invention provides a fluid dispenser for dispensing fluid for cleaning a person's hands, the dispenser comprising:

(a) a fluid containing reservoir, (b) a first pump to dispense fluid from the reservoir out a discharge outlet, (c) a drip tray located below the discharge outlet to catch fluid dispensed from the dispenser, and (d) a sensor mechanism, the sensor mechanism comprising a passageway with an inlet and an outlet, and a sensor at a location along the passageway, the sensor operative to detect a relative level of a contaminant, the inlet of the passageway in communication with the fluid caught in the drip tray, the sensor sensing contaminants in the fluid passed through the passageway.

BRIEF DESCRIPTION OF THE DRAWINGS

Further aspects and advantages of the present invention will become apparent from the following description taken together with the accompanying drawings in which.

DETAILED DESCRIPTION OF THE DRAWINGS

Figure 1:
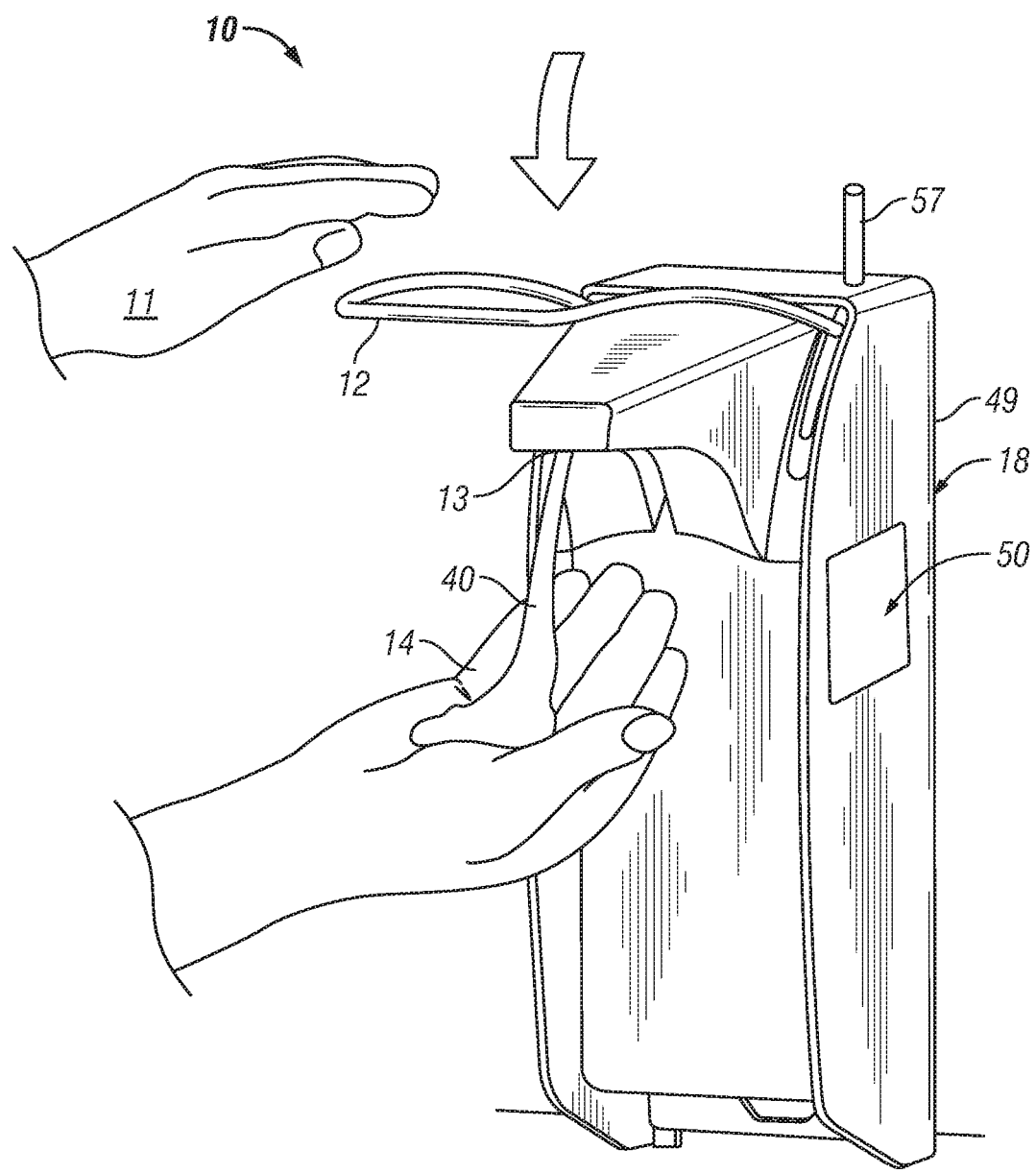
FIG. 1 is a perspective view of a soap dispenser in accordance with a first embodiment of the invention schematically shown as being manually used by a user to dispense hand soap.

Reference is made first to FIG. 1 which illustrates a first embodiment of a fluid dispenser 10 similar to that disclosed in U.S. Pat. No. 7,748,573 to Ophardt et al, issued Jul. 6, 2010, the disclosure of which is incorporated by reference. The dispenser 10 is adapted to be secured to a wall not shown. The dispenser 10 is schematically illustrated in FIG. 1 as adapted for manual activation as by a user using one hand 11 to urge a lever 12 downwardly so as to dispense fluid 40 from a nozzle 13 onto the palm of the other user's hand 14.

The dispenser 10 of this application differs from the dispenser disclosed in U.S. Pat. No. 7,748,573 notably in providing on a surface 49 of the side wall 18 of the housing 16, a sensor 50. The surface 49 of the side wall 18 is an exterior surface which is open to the environment about the dispenser. The sensor 50 is preferably a sensor capable of sensing contaminants from the environment about the dispenser which come to engage the sensor 50. The sensor 50 is preferably capable of detecting the presence of one or more contaminants on the sensor 50. The sensor 50 is preferably an electronic sensor requiring electrical power for its operation.

Figure 4:
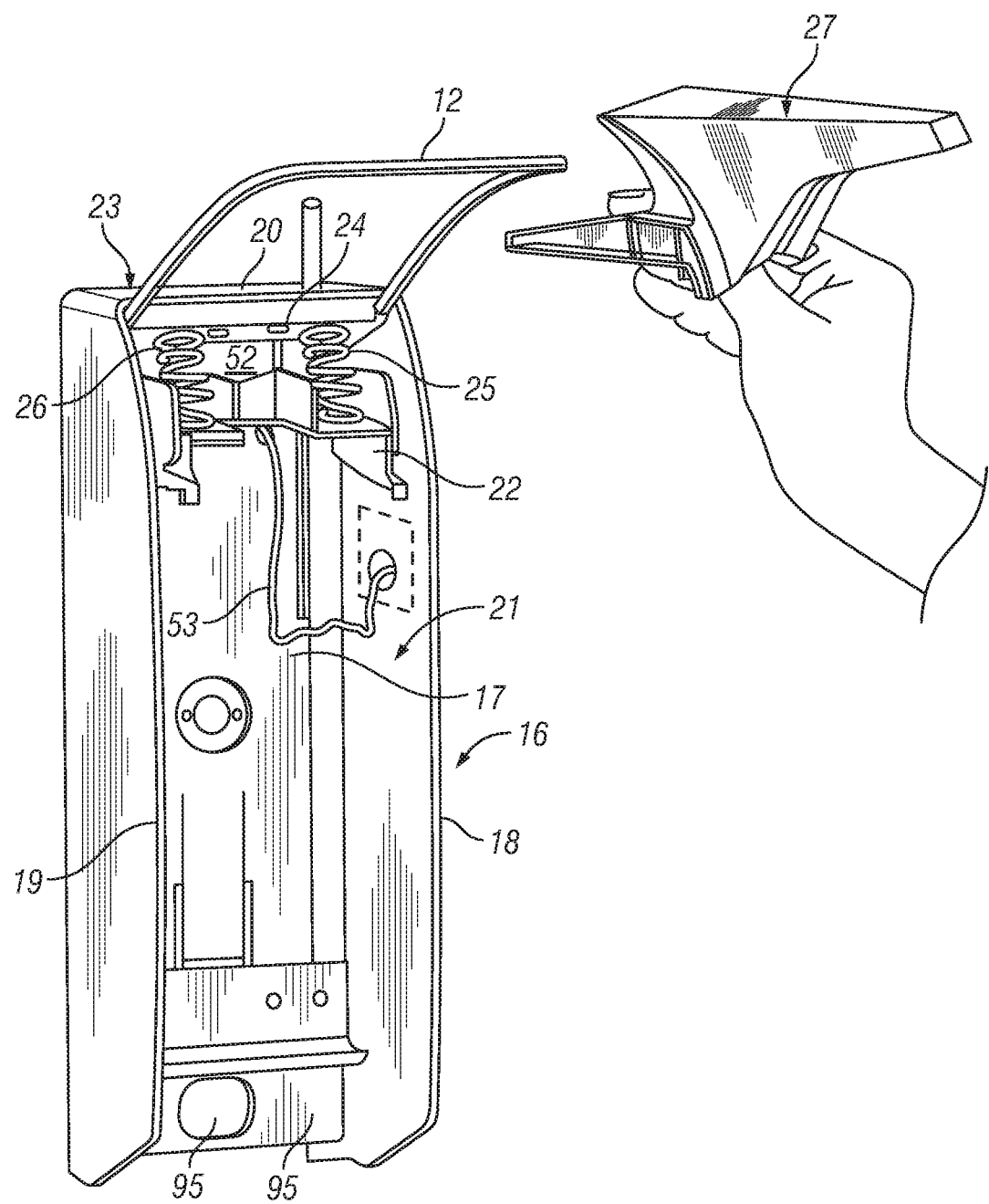
FIG. 4 is a perspective view of the dispenser shown in FIG. 1 with the nozzle shield removed.
Figure 5:
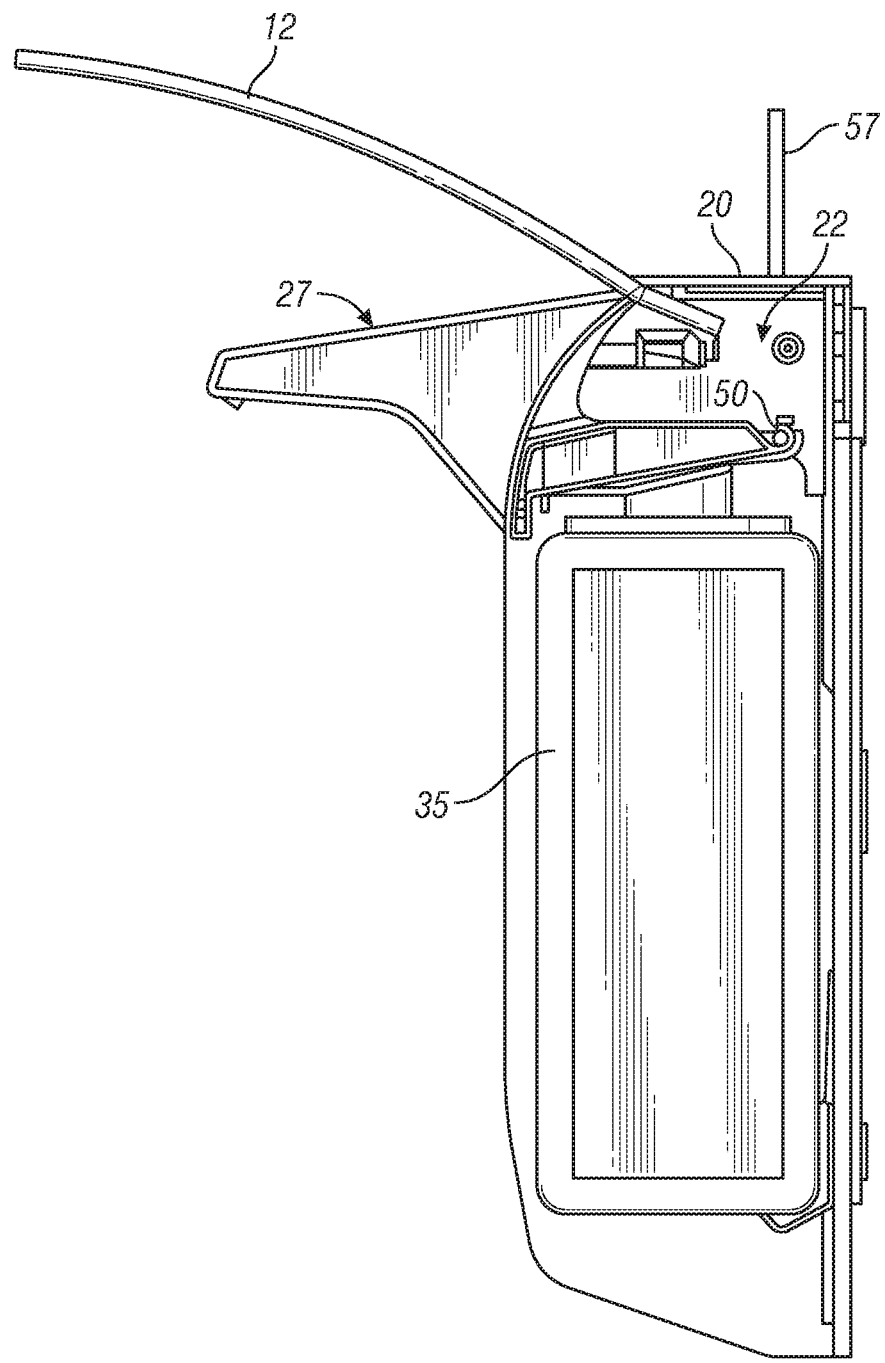
FIG. 5 is a schematic, partially cut-away cross-sectional side view of the dispenser in FIG. 1 with the nozzle shield in a closed position.
Figure 6:
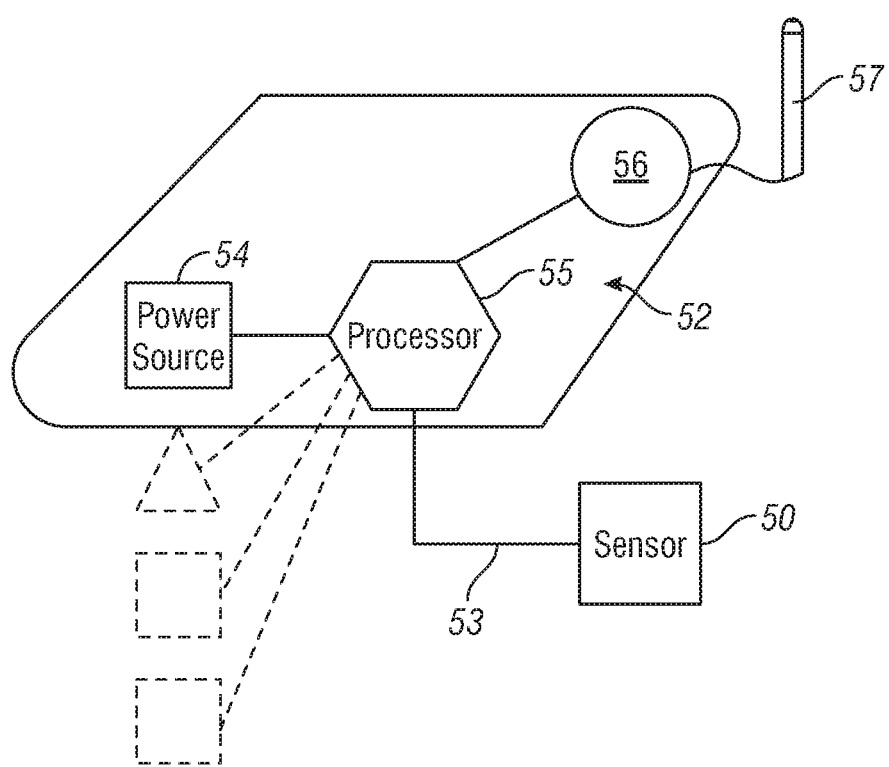
FIG. 6 is a schematic flow diagram showing electrically connected elements of the dispenser of FIG. 1.

Reference is made to FIG. 6 which schematically shows the sensor 50 and a control module 52 to control the sensor 50. The control module 52 is mounted to the housing 16 inside the upper interior of the housing as seen in FIG. 4 rearward of a support member 22 and springs 26 within a rear space proximate a back plate 17 underneath a top 20 and between the side wall 18 and an opposite side wall 19. FIG. 4 shows a conduit 54 connecting the sensor 50 to the control module 52.

In FIG. 6, the control module 52 is schematically illustrated as a circuit board which carries a processor 55, a communication device 56 and a power source 54. Each of the sensor 50, communication device 56 and power source 54 are connected to the processor 55. The processor 55 controls the receipt and distribution of power from the power source to the other electronic components and preferably the operation of these other components.

In operation, the sensor 50 is controlled by the processor 55 to at times as determined by the processor 55 to detect the presence of a contaminant on the sensor 50 and to generate a signal representative of the level of contaminant on the sensor 50. The processor 55 controls the communication device 56 so as to communicate as desired the signal and/or other data. The processor 55 in the preferred embodiment controls the communication device 56 so as to send the signal and/or other data to a remote electronic device. In the preferred embodiment the communication device including a wireless transmitter for which an antenna 57 is shown mounted externally on the top 20 of the dispenser 10.

Figure 7:
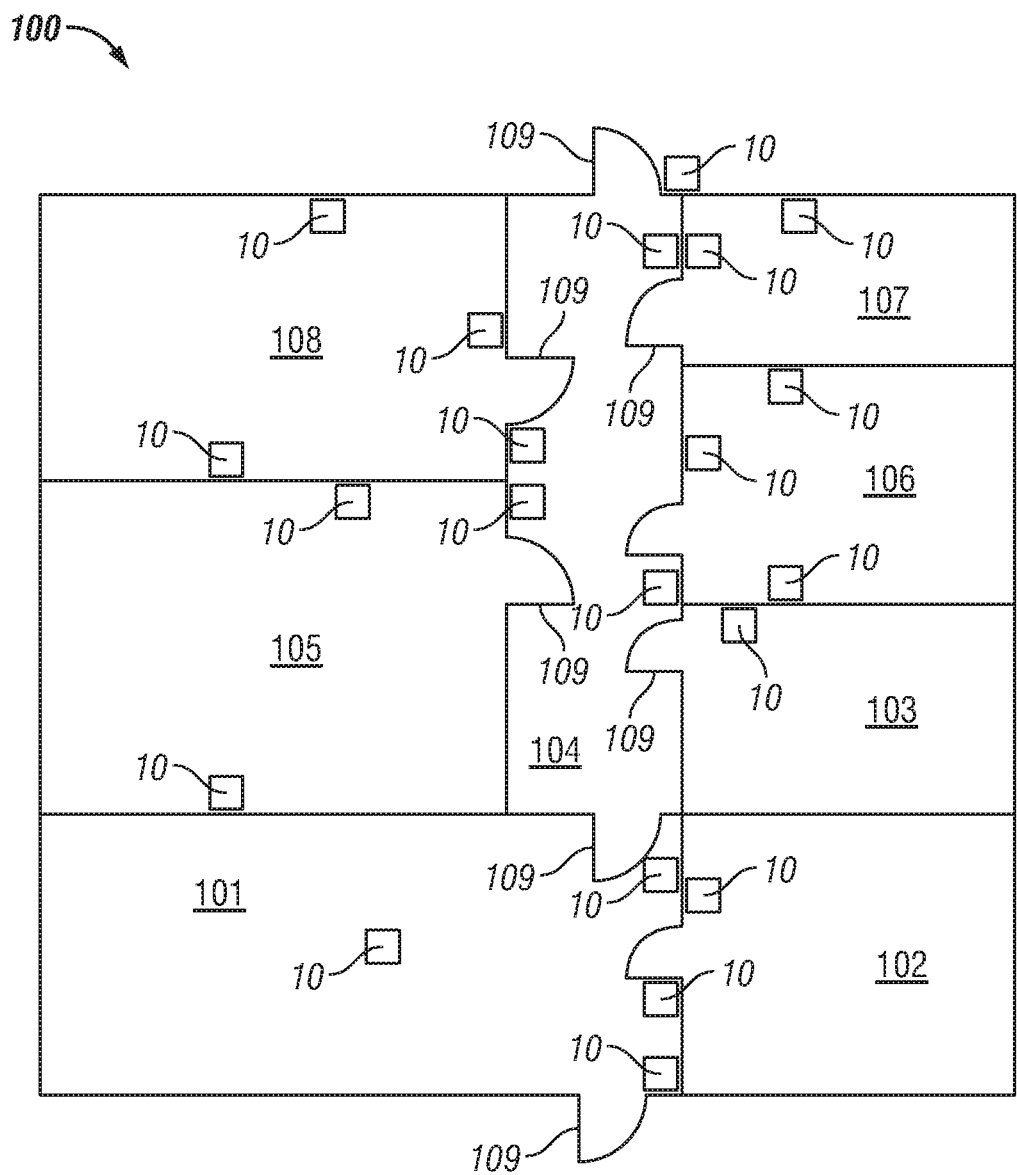
FIG. 7 is a plan view of a health care facility having an array of dispensers in accordance with the present invention.

Reference is made to FIG. 7 which shows a plan view of a health care facility 100 having a plurality of different dispensers 10 located at different locations within the facility 100. The facility 100 has a number of areas and rooms indicated as 101 to 108 with passage there between permitted by doors 109. The dispensers 10 are located at various different locations including those near the entry or exit of most doors 109, and within the rooms. The dispensers 10 may be mounted to the walls, on freestanding supports or supported on desktops, countertops and the like. Multiple dispensers may be in any room as, for example, in a washroom with multiple toilets or sinks or wash stations, not shown.

Figure 8:
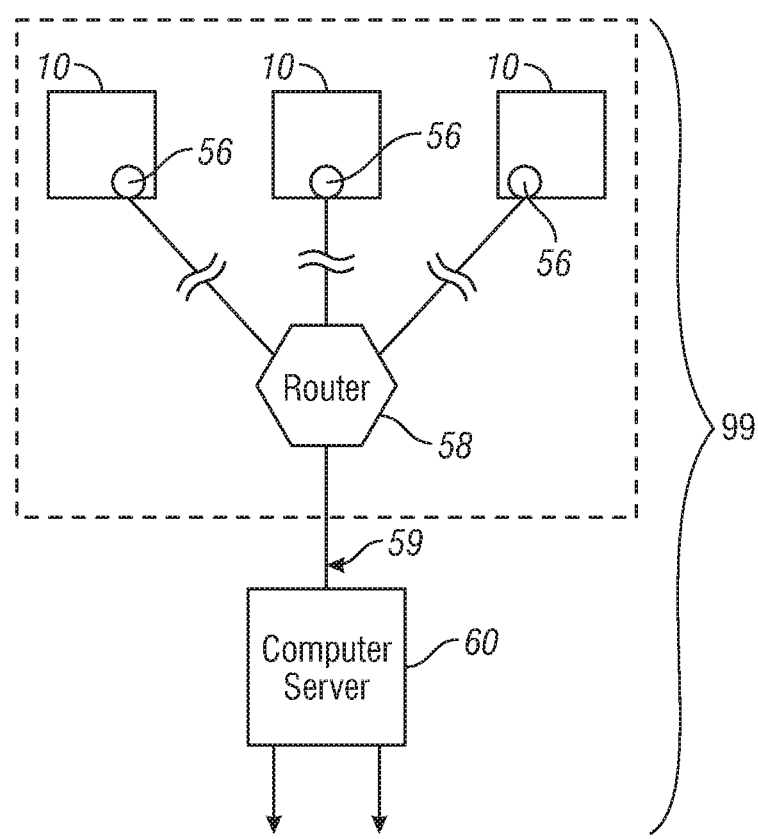
FIG. 8 is a schematic flow diagram showing a first arrangement for monitoring and control of the array of dispensers in accordance with the present invention.

Reference is made to FIG. 8 which schematically illustrates a contaminant sensing system 99. The system 99 includes the array of dispensers 10 from FIG. 7 but FIG. 8 shows for ease of illustration only three of the dispensers 10, each of which is schematically shown to have its respective communication device 56 wirelessly transmit information to a wireless router 58 which is connected to the Internet 59 which subsequently routes and transfers the information to a computer server 60.

The connection between each of the dispensers 10 and the router 58 need not be wirelessly and can be for one or more of the dispensers a hardwired connection. The preferred manner of communication from each dispenser 10 to the router 58 is wireless as, for example, preferably using a WiFi wireless system for communication between the communication device 56 and the router 58 which would comprise a WiFi router. The communication between the router 58 and the computer server 60 preferably is through the Internet. While FIG. 8 shows but three computers connected to a single router, it is to be appreciated that as many different dispensers 10 may be provided as desired for any facility 100 with each dispenser 10 communicating by a router and, of course, that a number of different routers 58 may be provided to service various of the dispensers 10. The router 58 is shown as being connected to one computer server 60, however, one or more different computer servers 60 may be provided, however, preferably, all of the information which may be gathered from any particular facility may be adapted to be consolidated and monitored at a single server or central processor.

The facility 100 may comprise any areas whatsoever including, for example, areas about or within one or more buildings, areas accommodating people, areas for processing of food, transport ships, and transportation terminals, or any portion thereof.

The communication between each dispenser 10 and the computer server 60 is not limited. Each or some of the dispensers 10 could communicate with other dispensers. One of the dispensers 10 could function as a router for other of the dispensers. Each or some of the dispensers 10 could communicate with message collection devices or directly to a computer as through a LAN as well as wireless router. Using the new IPV6 standard a dispenser 10 can be identified by its own IP address and can communicate to find a server in CLOUD and communicate information into the server in CLOUD. The communication is preferably provided at least one way from the dispenser 10 to the computer server 60, however, may also be two way with the dispenser 10 having capability to receive information from other devices, preferably from the computer server 60.

The particular manner that the signal from the sensor 50 is processed is not limited, and the signal may be processed in whole or in part in the dispenser 10 or in whole or in part in the computer server 60 or other remote processing device.

For example, in a first manner of operation, the processor in the dispenser 10 may send relatively unprocessed signals and data to the computer server 60 as to minimize processing within the dispenser 10 and thus reduce the need for processing capability and data storage in the dispenser 10. The computer server 60 would convert the signals and data received to data representative of the level of contaminant on the sensor 50. In a second manner of operation, the processor 55 in the dispenser converts the signal generated by the sensor 50 to data representative of the level of contaminant on the sensor 50, and communicates this data to the computer server 60. In a third manner of operation, the processor 55 in the dispenser converts the signal generated by the sensor 50 and its signal generator to data representative of the level of contaminant on the sensor 50. The processor 55 compares the level of contaminant sensed with one or more thresholds and makes ad determination as to whether the level of contaminant as sensed on the sensor exceeds one or more of these thresholds, and as well may provide a warning signal if the level of contaminant as sensed on the sensor is determined to exceeds one or more of these thresholds.

Referring to FIG. 4, the dispenser 10 includes the housing 16 having the back plate 17, the spaced side walls 18 and 19 and the top wall 20 which defining an interior 21 there between. The support member 22 is fixedly secured in the interior of the housing between the side walls 18 and 19 proximate the top wall 20. A lever mechanism 23 including the lever 12 and a lever bridge plate 24 is pivotally mounted to the support member 22. The lever springs 26 are disposed between the lever bridge plate 24 and the support member 22 so as to bias the lever 12 to an upper raised position.

Figure 2:
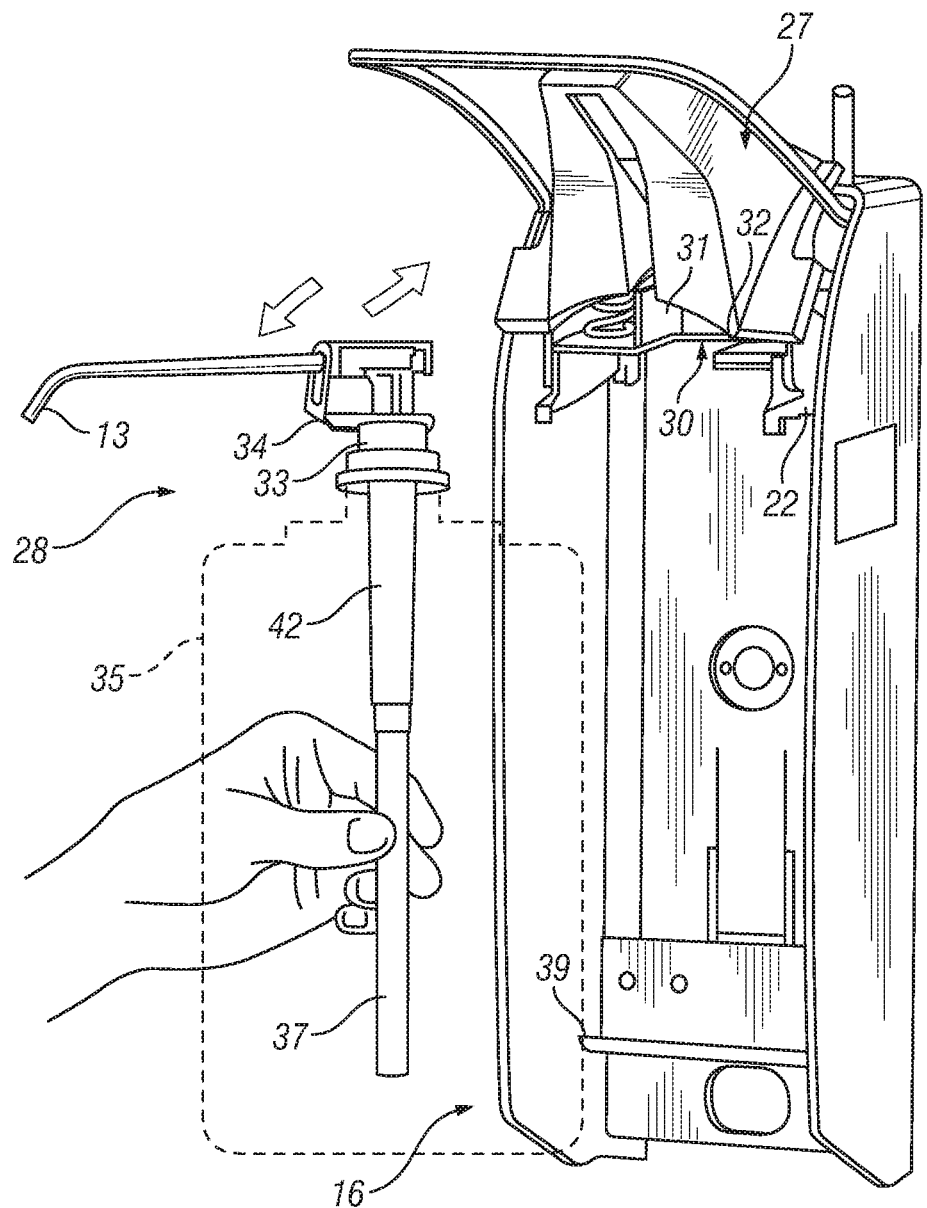
FIG. 2 is a perspective view of the soap dispenser of FIG. 1, however, with a nozzle shield in a raised, open position, the bottle removed and a pump mechanism being manually held by a user ready for insertion or removal.

FIG. 4 shows a nozzle shield 27 separate from the housing 16 and ready for manual coupling to the support member 22. FIG. 2 illustrates the dispenser 10 with the nozzle shield 27 coupled to the support member 22 and placed in a raised open position in which position the nozzle shield 27 permits a pump mechanism 28 to be coupled or uncoupled to the support member 22 by sliding forwardly or rearwardly. In this regard, the support member 22 carries a support plate with a central slot 30 open at a forward end. As seen in FIG. 2, vertical side walls 31 and 32 extend upwardly from the support plate 29 on each side thereof. The pump mechanism 28 is adapted to slide rearwardly into the central slot 30 with the slot 30 disposed about an enlarged radius cylindrical portion 33. A rectangular plate 34 is carried on the pump mechanism 28 above the cylindrical portion 33. The rectangular plate 34 is to be received above the support plate and located against rotation between the side walls 31 and 32.

Figure 3:
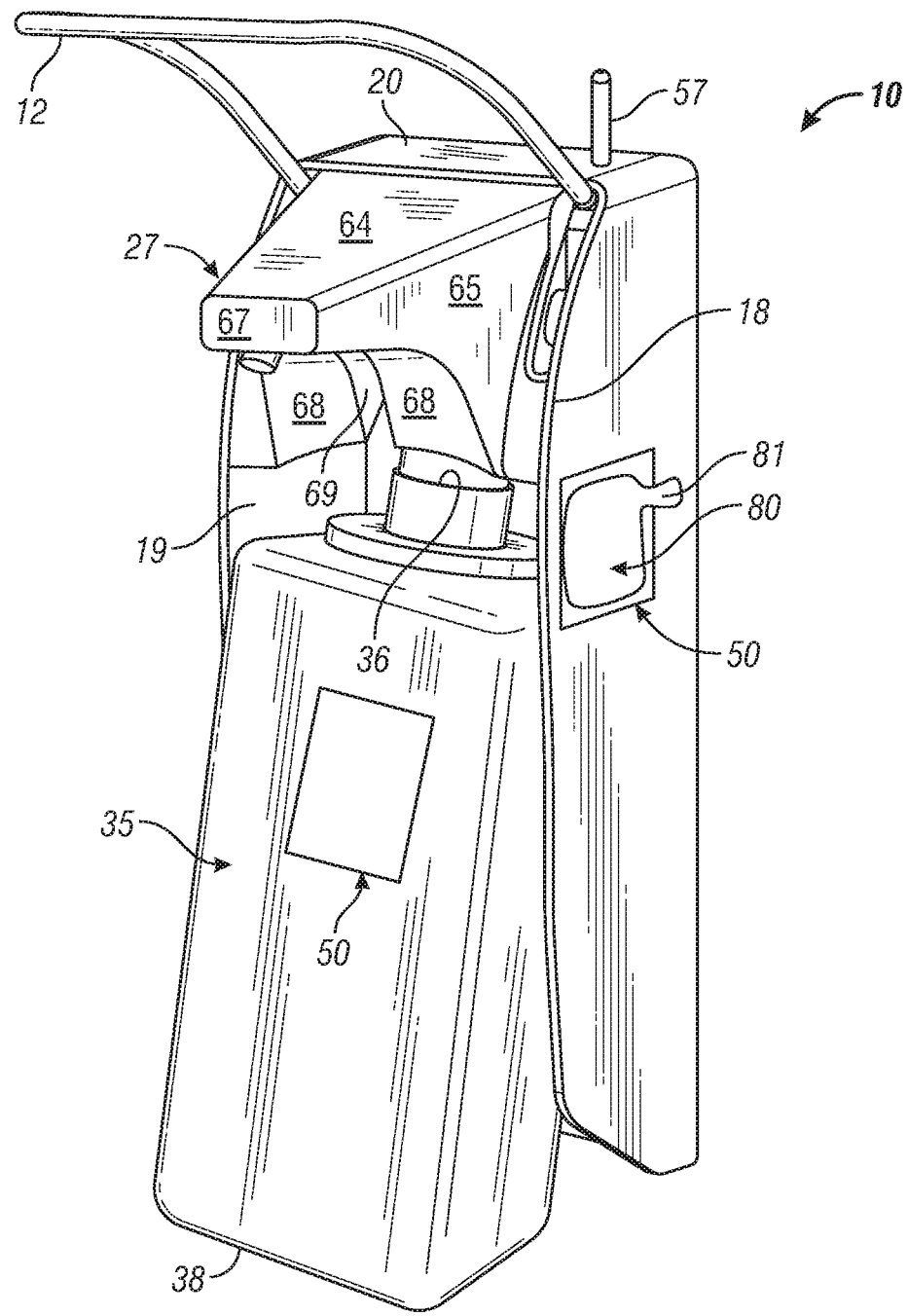
FIG. 3 is a perspective view of the soap dispenser of FIG. 1 in which the pump mechanism is coupled to the housing, the nozzle shield is in a closed position and a bottle is being replaced.

Reference is made to FIG. 3 which illustrates the dispenser 10 after the pump mechanism 28 has been applied as in FIG. 2 and the nozzle shield 27 moved from the raised open position of FIG. 2 to the closed position seen in FIG. 3. A bottle 35 with an open upper end 36 may be, when disposed at an angle, placed to have a dip tube 37 of the pump mechanism 28 inside its open end 36 and the bottle 35 then slid upwardly between the side walls 18 and 19 of the housing 16 upwardly about the dip tube 37 to a position where a bottom 38 of the bottle is disposed above a height of a support ledge 39 secured across the back of the housing 16. The bottom 38 of the bottle 35 may then be pushed rearwardly to rest on the support ledge 39. The bottle 35 serves as a removable and replaceable reservoir for the fluid to be dispensed. With the bottle 35 inserted and in the position, for example, as illustrated in FIG. 1, pressing downwardly on the lever 12 will dispense fluid 40 out of the nozzle 13 of the pump mechanism 28. The pump mechanism 28 preferably comprises a piston pump assembly with the nozzle 13 comprising a forward hollow tubular extension from a piston 41 which is slidable within a piston chamber forming element 42 which has liquid fed to it from the bottle 38 via the dip tube 37. The piston 44 is reciprocally vertically displaced by the lever mechanism 23 to pump fluid. FIGS. 2 and 3 show in solid lines one configuration in which the bottle 35 may be replaced independently of the pump mechanism 28, FIG. 2 schematically illustrates, in dashed lines, a bottle 35 mechanically secured to the pump mechanism 28 forming together a replaceable unit that can as a unit be coupled to and uncoupled from the dispenser for al removed and replacement as a unit via the forward access provided to the interior 21 of the housing 16 when the nozzle shield 28 in a raised open position as seen in FIG. 2. The replaceable unit comprising the bottle 35 and the pump mechanism 28 is preferably disposable when empty.

The preferred embodiment of the dispenser 10 shown in FIGS. 1 to 5 illustrates a single sensor 50 carried on the exterior surface 49 of the side wall 18. Sensors similar to the sensor 50 sensor 50 may be provided at other locations on the dispenser 10, including, for example, on an inside surface of the side wall 18; on an inside or an outside surface of the side wall 19, on the upper surface of the top 20, and on the nozzle shield 27 as, for example, on any of a top surface 64, side surface 66, front end surface 67 or under surfaces 68; on the activation lever 12, on the pump mechanism 28 and on the bottle 35. A sensor could be provided on the lever 12 preferably on a forwardmost horizontal portion 70 of the lever 12 which is most likely to be contacted by the hand of a user. A sensor could be provided on the nozzle 13 preferably proximate where a fluid is discharged and there may be a likelihood of either contact by a user's hand or growth of biological contaminants.

The sensor may be provided secured to components of the dispenser 10 which are typically not replaced and such a sensor would need to have a relatively long useful life. The sensor may, however, be provided to be removable and replaceable from the dispenser 10 so as to permit the use of a sensor whose sensing activities are only effective for a period of time or which degrades with time as, for example, as contaminants come to engage the surface of the sensor. In this regard, the sensor 50 of the preferred embodiment of FIGS. 1 to 5 preferably is a replaceable sensor as, for example, comprising a replaceable member which can be secured to the side wall 18 and releasably electrically connected to the control module 52 by the provision and use of a manually engageable end releasable plug 61 on the conduit 53 which releasably connects the sensor 50 to the control module 52. In the preferred embodiment, the sensor 50 comprises a relatively flat planar member to be adhesively secured to the wall 18 with a release adhesive permitting later removal of the sensor 50. As seen in FIG. 4, an opening 62 is provided through the wall 18 behind the sensor 50 through which the conduit 53 is passed to provide for connection of the sensor 50 shown in dashed lines in FIG. 4 to the control module 52. Such as removable and replaceable sensor 50 may, for example, be provided in a kit with a replacement bottle 35 with a user on replacing an empty bottle 35 at the same time, manually replacing the sensor 50 with a new replacement sensor. The sensor 50 may, for example, be coupled to a replacement bottle 35 such that the removal of a closure on the bottle 35 to permit its insertion and use on a dispenser 10 also requires removal of the new sensor 50.

Wherever the sensor 50 is located on the dispenser 10, it is within the scope of a person skilled in the art to provide a method for providing electrical power to the sensor 50 from the control module 52 to the site of the removable sensor 50 and to provide a mechanism for easy electrical connection. For example, at a location where any sensor is to be provided, electrical contact pads may be provided on the dispenser 10 to engage electrical contact pads carried on the sensor. Insofar as the sensor 50 is desired to be secured to the handle 12, insofar as the handle 12 is a hollow tube, then electric wiring can extend internally within the handle to a location where the sensor 50 is to be located. The handle 12 may be made from a left half portion and a right half portion, each as a metal rod or tube, and with a plastic spacer in the center of the forwardmost horizontal portion 70 which mechanically connect the two metal halves together while electrically separating them. A sensor could be provided with a first electrical contact pad to engage the left half portion and a second electrical contact pad to engage the right half portion and thus the sensor will bridge between the two metal halves and complete an electrical conduit between the rear ends of each of the metal halves which are each to be electrically connected to the control module 52.

Preferably, a sensor timing arrangement is provided which will determine the time when a sensor is initially activated so as to first permit contaminants engage on its surface and with the sensor timing arrangement including a timing device such that signals from the sensor representative of the level of contamination of the sensor are provided with an indication as to relative time and the time from initial activation. Such a timing arrangement may arise, for example, in the embodiment of FIGS. 1 to 5 with the processor 55 including a timer and a capability to sense when the plug of a new sensor 50 is first connected to the control module 52. While not necessary, it is preferred that each sensor 50 may have an identification number and the control module 52 have a capability to determine the identification number of each sensor 50 and to determine the first time when any particular sensor 50 is sensed as being electrically connected and/or initially activated. Preferably, the sensor 50 may have some protective mechanism to prevent contaminates from becoming engaged on the sensor 50 prior to electrical connection of the sensor and or activation. As schematically illustrated in FIG. 3, a protective release sheet 80 is provided over the sensor 50 which release sheet 80 has a tab 81 to be manually engaged to remove the release sheet after electrical connection of the sensor 50 to the control module 52. By removing the release sheet 80, the sensor 50 would be initially activated, meaning that the surface of the sensor 50 would first come to become open to being engaged by contaminants. The removal of the release sheet 80 and the initial activation of the sensor 50 could be assumed to occur at substantially the same time that the sensor 50 is electrically connected to the control module 52.

As another arrangement, the release sheet 80 could include an element which blocks electrical connection of the sensor 50 to the control module 52 or otherwise prevent the operation of the sensor 50 until such time as the release sheet is removed. With such an arrangement, removal of the release sheet 80 would initially activate the sensor 50 after the sensor 50 was previously electrically connected to the module 52. This would permit the dispenser 10 to have the sensor 50 removably attached with the release sheet 80 in place to be shipped and transported ready for use by installation of the dispenser 10 and removal of the release sheet 80.

The sensor 50 shown in FIG. 3 is a relatively thin planar member which can be releasably secured to the side wall 18 as by a releasable adhesive on the rear of the sensor 50. The release member 80 is preferably a thin sheet, for example, of plastic material which may be secured as over the forward surface of the sensor 50 by an adhesive, at least with the adhesive about a periphery of the front surface of the sensor so as to avoid sensory areas on the sensor which contaminants are to engage and be sensed. The sensor 50 preferably has electrical components and circuitry printed thereon. The release sheet 80 may have electrical components and circuitry printed thereon to be coupled with the electrical components and circuitry on the sensor 50 to blocking operation of the sensor 50 until the release sheet 80 is removed.

Various sensors are known which would be useful as a sensor 50 in accordance with the present invention. A sensor could be used which accurately senses the presence of one or more specific contaminants. Such sensors are often expensive and have difficulties in respect of accuracy and calibration. In the context of an arrangement in accordance with the present invention in which an array comprising a plurality of dispensers is provided within a facility, the invention permits the use of sensors which may not individually be accurate in predicting the presence of a contaminant. In accordance with the present invention, by providing an array of dispensers 10 in which a number of dispensers 10 are used in a facility 100, sensors 50 may be used which may not be considered particularly accurate or relatively accurately calibrated. Preferably, in accordance with the present invention, the array of dispensers 10 provided is in a facility in a relatively large number of dispensers. The number of dispensers is preferably at least 25 and, more preferably, at least 50, at least 100, at least 200, at least 300, at least 400, at least 500 and, more preferably, at least 1000 dispensers. In accordance with the present invention, it is preferred that a relatively large number of the dispensers 10 are included in the array within the facility 100. The opportunity to have such a large number of arrays of dispensers 10 in a facility is readily achievable as, for example, in health care facilities and hospitals and where large number of dispensers is provided in relatively small areas. Insofar as the dispensers 10 carrying the sensors 50 are manually operated dispensers, there is an easy opportunity for easily providing large numbers such dispensers 10 in an array in the facility.

In many environments such as hospitals where there are concerns about contaminants, particularly biological contaminants, it is desired that the bottles 35 containing the fluid to be dispensed be changed relatively frequently, particularly where there is an opportunity or necessity for the dispenser to be engaged by a user in dispensing the fluid, and the dispenser may serve as a location for the deposit, and transfer to others of contaminants. Preferably, each bottle 35 is replaced about every 14 to 30 days whether or not the bottle is empty of fluids. Such bottles 35 have preferred volumes in the range of 500 ml to 2 litres. A preferred bottle 35 has a volume of 500 ml which in many hospital and health care environments will result in the bottle, when placed in areas of a facility with average usage being typically emptied and replaced every two to three weeks. The bottles 35 are also preferably available in larger sizes such as 1 litre and greater, which are advantageous for insertion into dispensers 10, in relatively high use areas, such that the bottles 35 may be expected to be emptied within one to four weeks. Preferably, a new replacement sensor 50 is provided and replaced each time the removable bottle 35 is replaced. In such an arrangement, the replaceable sensor 50 need only have, at most, a useful life which is the useful life of the average bottle which typically does not exceed two to four weeks. Providing a sensor 50 which would be active for merely two to four weeks would be useful in accordance with the invention of the present application and, again, facilitate the selection of a sensor by eliminating the need for long term useful sensing.

Moreover, in accordance with the present invention, in one preferred embodiment, the replaceable sensor 50 may only be useful to sense contamination for a relatively short period of time such as, for example, selected from a time period of a number of minutes, or hours, or days or weeks after activation. For example, a sensor might have a useful sensing life of but a few minutes, say, for example, 5, 15 or 30 minutes or, for example, one, two, six, twelve, eighteen, twenty-four hours or thirty-six hours or two days, three days, four days, five days, six days or seven days or some time period, for example, between one day and fourteen days.

The preferred sensor 50 in accordance with the present invention is a sensor capable of sensing contaminants on the sensor. In the case of biologic contaminants, the presence of the biologic contaminants on the sensor 50 may increase with time as the biologic contaminants may grow and remain engaged on the sensor 50. Signals indicating the level of contaminants on the sensor may be provided over time from the time of activation onward. The speed at which the level of contaminants increase can be measured on the sensor during its useful life as one factor to indicate the relative level of contaminants in the environment about the dispenser. As an example of an array of dispensers 10 in accordance with the present invention, 1000 dispensers 10 can be provided in a hospital facility. Each sensor 50 with the various individual dispensers 10 will be replaced periodically and preferably randomly, upon replacement of the bottles 35. Each dispenser 10 will provide data information to the central computer server 60 including the time when each sensor was initially activated, and levels of contaminant sensed at various times after initial activation. From such data, amongst other items, the speed at which the level of contaminant changes typically increases can be determined. The data received from the 1000 dispensers 10 can be subjected to various data manipulation techniques such as statistical analysis, and averaging including techniques to disregard, for example, readings from sensors which are within either a bottom percentile of contamination level readings for all comparable dispensers such as, for example, in the bottom 10% or above a certain percentile of contamination level readings for all comparable dispensers such as above 90%. The data may be collected from the dispensers 10 in the facility 100 over a period of time such as over a three, six or twelve month period of time to establish expected baselines and establish thresholds against which future data can be compared. Thereafter, data monitored from the array of dispensers as a whole and, as well, from individual groups of dispensers within the array or individual dispensers may be compared to the historical values to assist in generalized determinations as to whether or not there may be an increase in contaminants in the facility as a whole or certain areas in the facility or even at certain dispensers. Such data can serve as an early warning system towards giving notice and early warning of increasing contaminants. Data gathered from one facility such as a first hospital may be compared to data from another facility such as a second hospital.

Various algorithms such as statistical assessments will be apparent to a person skilled in the art as useful towards assessing the data received from the dispensers towards developing thresholds and assessing when reasonable thresholds for levels of contaminants have been exceeded or levels of contaminants are at acceptable levels.

The sensor 50 may be adapted to sense one or more contaminants. A preferred sensor may be a relatively simple sensor which is adapted to sense one contaminant or type of contaminant. While there may be known contaminants which are of a particular concern as in a hospital environment such as Methicillin-resistant *Staphylococcus aureus* (MRSA), a type (strain) of staph bacteria that does not respond to some antibiotics that are commonly used to treat staph infections and *Clostridium difficile* (*C. difficile*) bacteria and while it would be preferred to use a sensor which would sense for the presence of any particular pathogen, this is not necessary for the invention to be carried out. One preferred embodiment of the invention is to utilize a sensor which senses an indicator contaminant which is reasonably expected to have a correlation to a contaminant of concern without directly sensing contaminant of concern. For example, in a hospital environment, while it might be difficult to have a sensor which senses MRSA, insofar as other biologic contaminants such as common *E. coli* bacteria are sensed, an increase in the level of *E. coli* bacteria is reasonably to be expected to be correlatable to a rise in other dangerous contaminants such as MRSA and *C. difficile*. A sensor for *E. coli* or other indicator contaminant which is more readily available and less expensive comprises a reasonable sensor to be used toward assisting and indicating general levels of contamination within a hospital facility and may be demonstrated by historical data to having a correlation to other unsensed contaminants. As another example, rather than sense bacteria, micro-organisms or plants directly, signalling moleculars produced by the bacteria, micro-organisms or plants may be sensed as methods of detecting the bacteria, micro-organisms and plants as in a manner described in U.S. Pat. No. 7,651,843 to Stubbs et al, issued Jan. 26, 2010, the disclosure of which is incorporated herein by reference.

In FIG. 6, the control module 52 is shown as including a power source 54. One preferred power source is a removable and replaceable battery. The nature of the power source 54 to be used is not limited and would include, for example, mechanisms to generate power and mechanisms to store the power. Mechanisms to generate power can include light powered generators, such as solar generators, and generators which provide power on a user manually activating the dispenser as by moving the lever 12.

Figure 9:
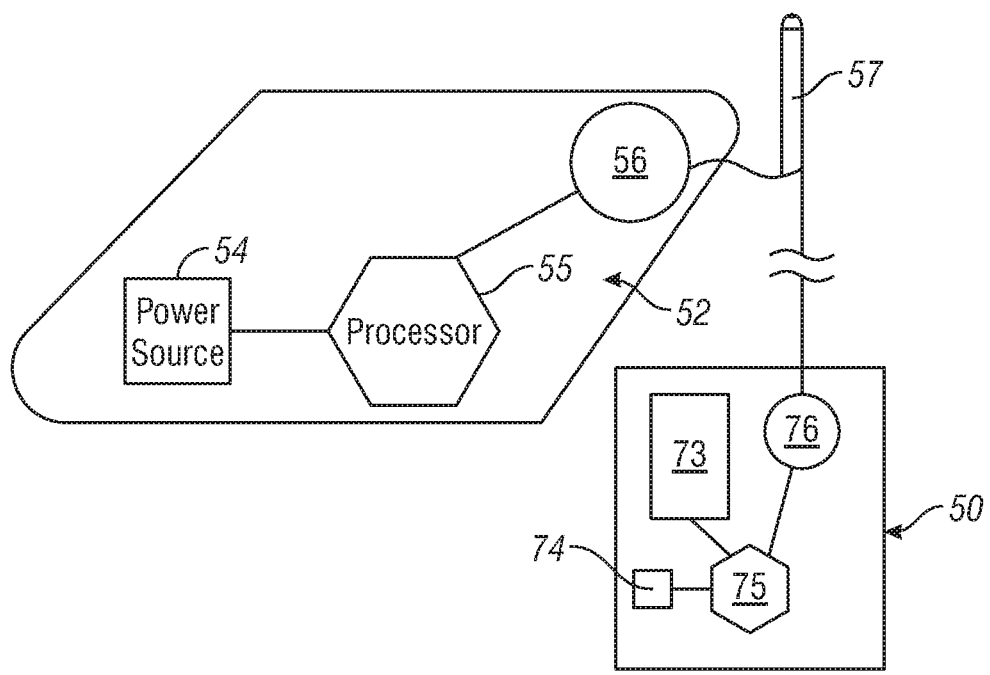
FIG. 9 is a schematic flow diagram similar to FIG. 1 but showing a different configuration of electrically powered elements of the dispenser of FIG. 1.

In the embodiment illustrated in FIG. 6, the sensor 50 is hardwired to the control module 52 and receives electrical power from the control module 52. Reference is made to FIG. 9 which shows an alternate arrangement for the connection of the control module 52 and the sensor 50. In the embodiment of FIG. 9, the sensor 50 is illustrated as a wireless sensor 50 having electrically connected elements comprising a sensor processor 75, a sensor communication device 76, a sensor power source 74 as well as a contaminant sensing mechanism 73. The sensor power source 74 preferably is a battery. The sensor communication device 76 is adapted to wirelessly communicate with the communication device 56 on the control module 52. The nature of the wireless communication between the control module 52 and the sensor control device 76 is not limited but can preferably provide but one-way communication from the sensor 50 to the control module 52. The wireless communication between the control module 52 and the sensor control device 76 is preferably over but a very short distance. One preferred method of communication would be WiFi wireless communication. The communication device 56 of the control module 52 may use different wireless communication systems to communicate with the sensor communication device 76 than with other remote devices such as the wireless router 58.

The combination of the wireless sensor 50 and the control module 52 as shown in FIG. 9 can advantageously be used as, for example, in the embodiment illustrated in FIGS. 1 to 6 so as to, for example, avoid the need for a hardwired communication between the sensor 50 and the control module 52 and thus eliminate, for example, the conduit 53 and its plug as shown in FIG. 4. Use of a wireless sensor 50 can facilitate the location of a sensor at virtually any location on the dispenser 10 and its components and facilitate the installation and removal of any sensor which is to be removable and replaceable. Insofar as the wireless sensor 50 is carried on the dispenser 10 in relative close proximity to the control module 52, the battery serving as the power source 77 for the wireless sensor need not have any substantial capacity to power communication. Preferably, in an arrangement as shown in FIG. 9, the wireless sensor would be located within, at most, twelve inches, more preferably, at most, six inches or three inches from the control module 52. The arrangement illustrated in FIG. 9 is readily adapted for substitution for the sensor 50 and control module 52 as in FIG. 4 eliminating the need for the hardwired conduit 53.

As another embodiment of the dispenser 10, a wireless sensor 50 as illustrated in FIG. 9 could be provided in the dispenser 10 and communicate as, for example, wirelessly with the wireless router 58 as shown, for example, in FIG. 8. In such a case, the control module 52 could be eliminated from the dispenser, however, the sensor processor 75 in that case would need to have the capability of controlling the sensor 50 and its operation and suitably transmitting acceptable signals and data to the router 58. Thus control module 52 could be eliminated from the dispenser 10 or at least not serve a purpose in the control of or communication with the sensor 50.

Figure 10:
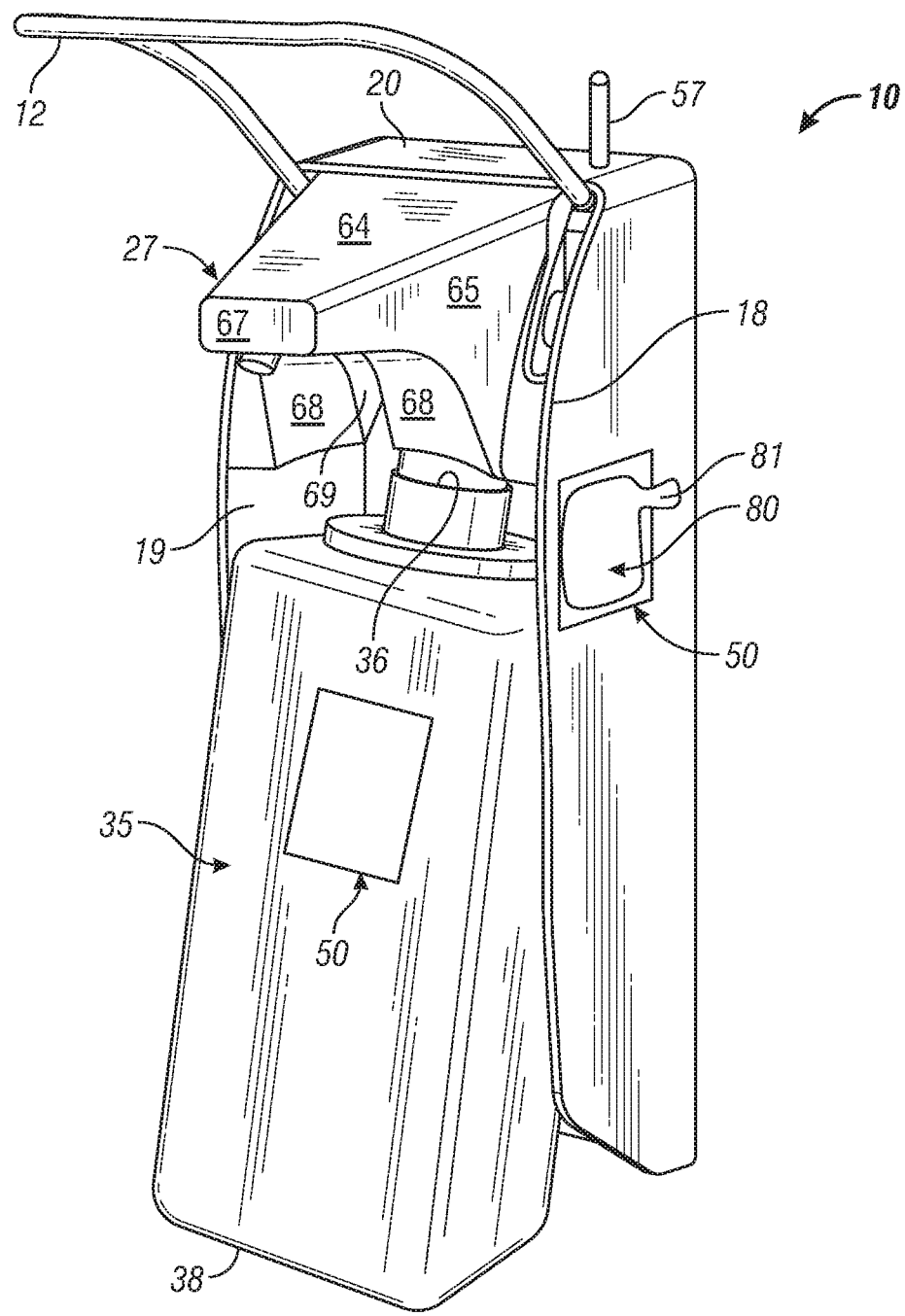
FIG. 10 is a perspective view of a soap dispenser similar to that shown in FIG. 3 but with a modified bottle.

Reference is made to FIG. 10 which is identical to FIG. 3, however, shows a second sensor 50 as applied to the bottle 35 on a front surface 80 of a front wall 81 of the bottle 35. The sensor 50 shown in FIG. 10 on the bottle is preferably a wireless sensor of the type illustrated in FIG. 9 which may be provided in combination with a control module 52 of the type shown in FIG. 9 carried internally within the dispenser for communication between the wireless sensor 50 on the bottle and the control module 52 (not shown in FIG. 10) or, alternatively, the sensor may comprise a stand alone sensor 50 of the type illustrated in FIG. 9, however, with capability of transmitting directly from the sensor 50 on the bottle to the wireless router 58 shown in FIG. 8. FIG. 9 continues to show a first sensor 50 on the side wall 18 of the dispenser 10 in addition to the sensor 50 on the bottle 35, although only one sensor is necessary.

Figure 11:
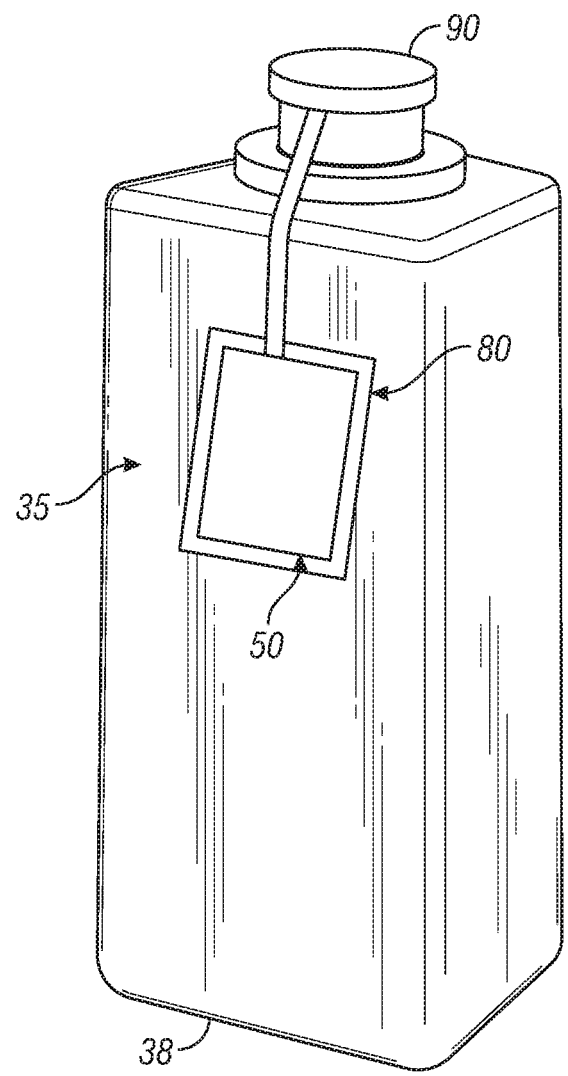
FIG. 11 is a perspective view of the bottle shown in FIG. 10 prior to coupling to the dispenser.

FIG. 11 shows the bottle 35 used in FIG. 10, however, prior to coupling of the bottle to the dispenser with the bottle carrying a removable snap-off cap 90 sealing the opening to the bottle 35. The sensor 50 is shown as covered by the transparent removable release sheet 80 which on removal activates the sensor 50. The cap 90 needs to be removed prior to coupling of the bottle to the dispenser. A strap 91 mechanically couples the cap 90 to the release sheet 80 such that with removal of the cap 90 for use of the bottle 35, the release sheet 80 is automatically removed.

Figure 12:
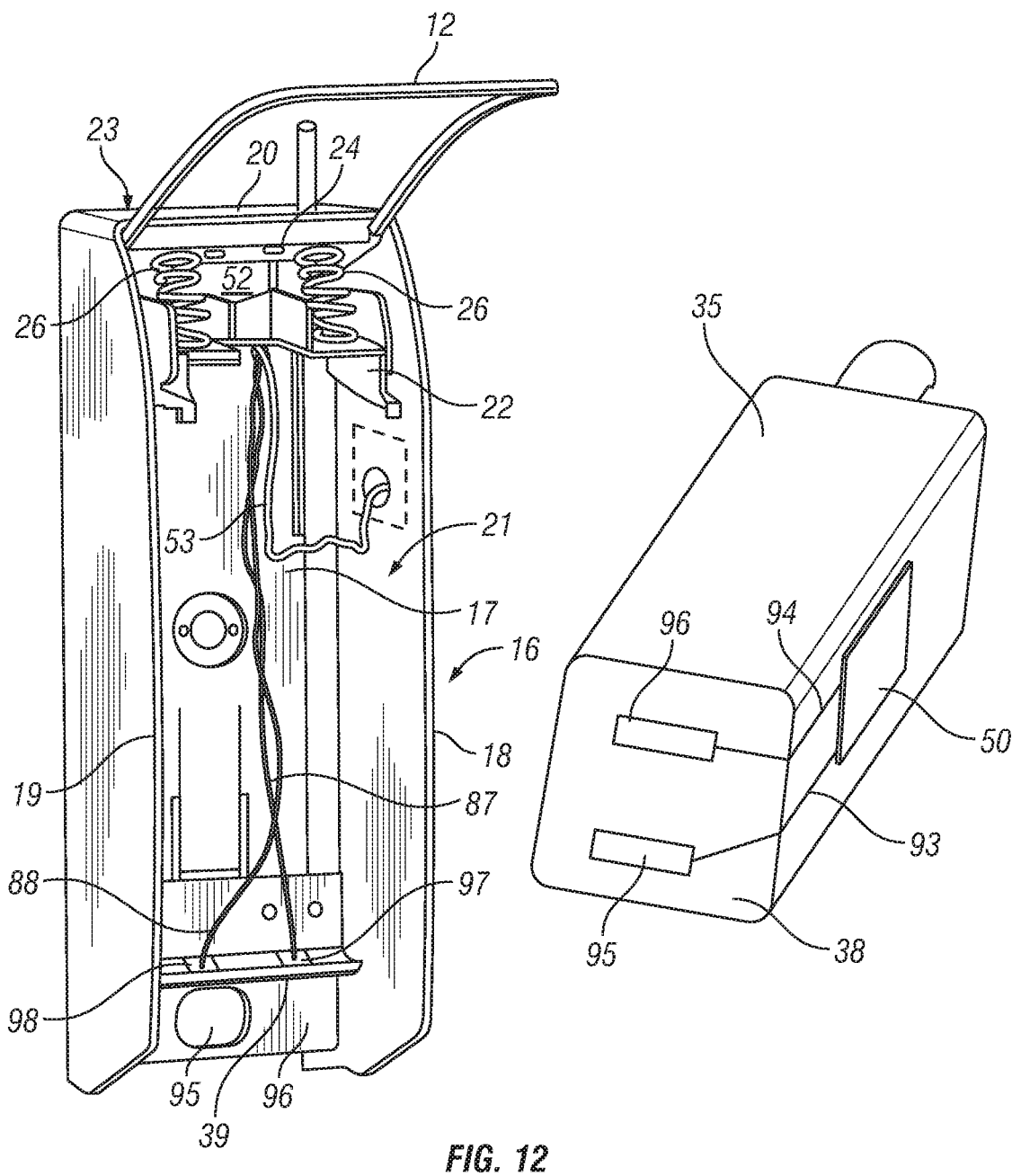
FIG. 12 is a partial schematic pictorial view showing a modified bottle added to the dispenser housing with complementary electrical touch pads for electrical connection on coupling the bottle to the dispenser.

Reference is made to FIG. 12 which illustrates a dispenser 10 similar to that shown in FIG. 4 but in which a wired sensor 50 is provided on the front surface of the bottle 35 and in which connection wires 93 and 94 extend from the sensor 50, each to a respective metal electrical contact pad 95 and 96 provided on the bottom 38 of the bottle. Corresponding electrical contact pads 97 and 98 are provided on a support ledge 39 secured across the back of the dispenser housing 16. When the bottle 35 is engaged on the housing in the manner as seen in side view in FIG. 5, the contact pads 95 and 96 of the wireless sensor 50 carried on the bottle 35 will make electrical contact with the contact pads 96 and 97 on the support ledge 39. The contact pads 96 and 97 on the support ledge 39 have connection wires 87 and 88 which extend to the control module 52. This arrangement of FIG. 12 provides for a removable bottle 35 with the sensor 50 attached to the bottle 35 and adapted to be hard wired to the control module 52 when the bottle 35 is engaged to the dispenser 10.

FIG. 10 shows two sensors 50 on the dispenser, namely the sensor 50 on the side wall 18 of the dispenser 10 in addition to the sensor 50 on the bottle 35, although only one sensor is necessary. In accordance with the present invention, one, two, three or more sensors may be provided on the same dispenser. The various sensors 50 may be hardwired in an arrangement as illustrated in FIG. 6 or wireless as in an arrangement in FIG. 9. Some of the sensors may be hardwired and others may be wireless.

FIG. 2 schematically illustrates a replaceable unit comprising not only the bottle 35 but also the pump 28 securely attached thereto. As in the manner illustrated in FIG. 10 or FIG. 12, a sensor 50 may be provided on the bottle 35 of the replacement unit shown in FIG. 2 comprising the bottle 35 together with the pump 28. In another embodiment of such a replaceable unit, a sensor 50 can be applied onto the nozzle 13 and removable with the replaceable unit.

Reference is made to FIGS. 13, 14, 15 and 16 showing a dispenser in accordance with a second embodiment of the invention.

Figure 14:
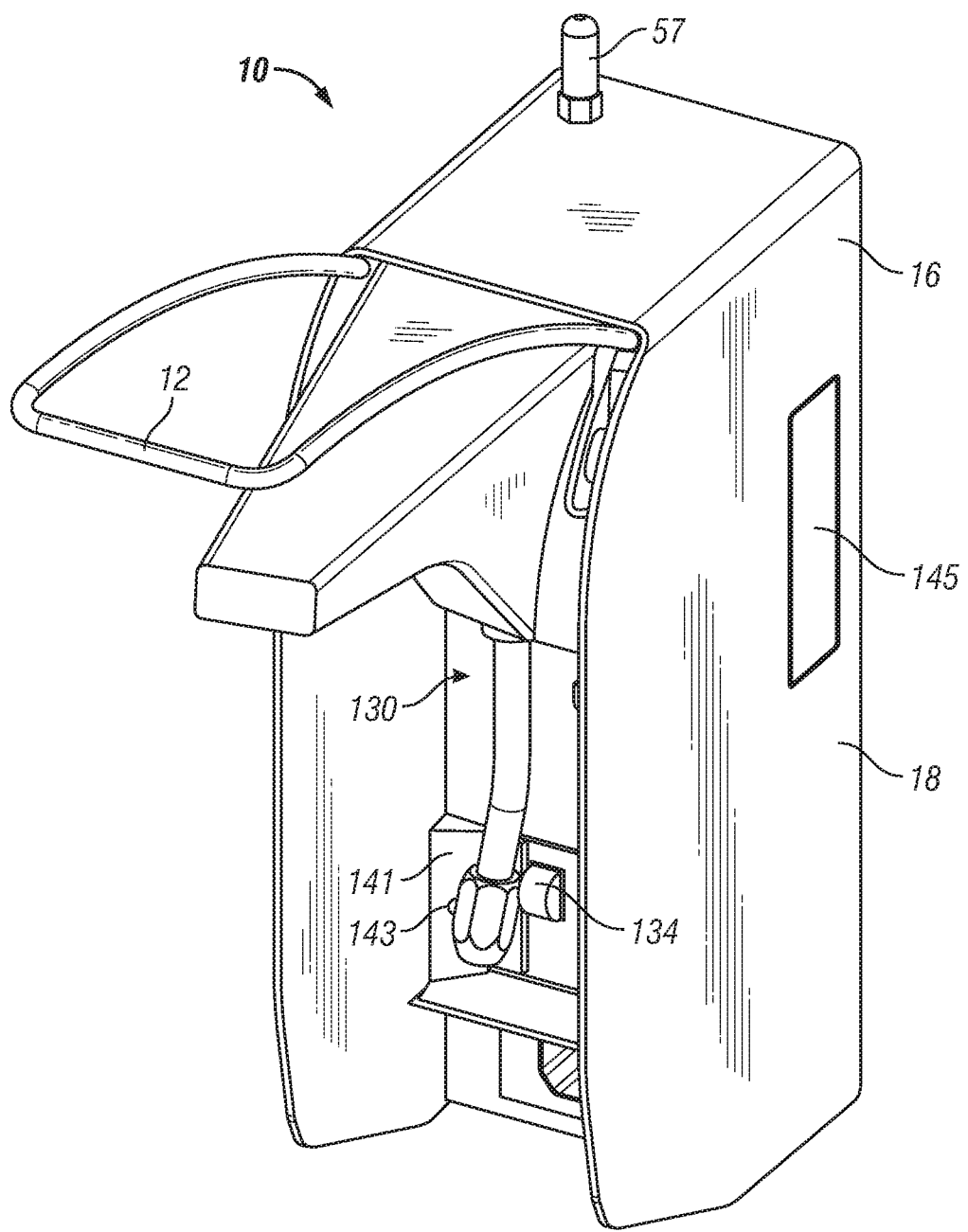
FIG. 14 is a front perspective view of the dispenser of FIG. 13 with the bottle removed.
Figure 15:
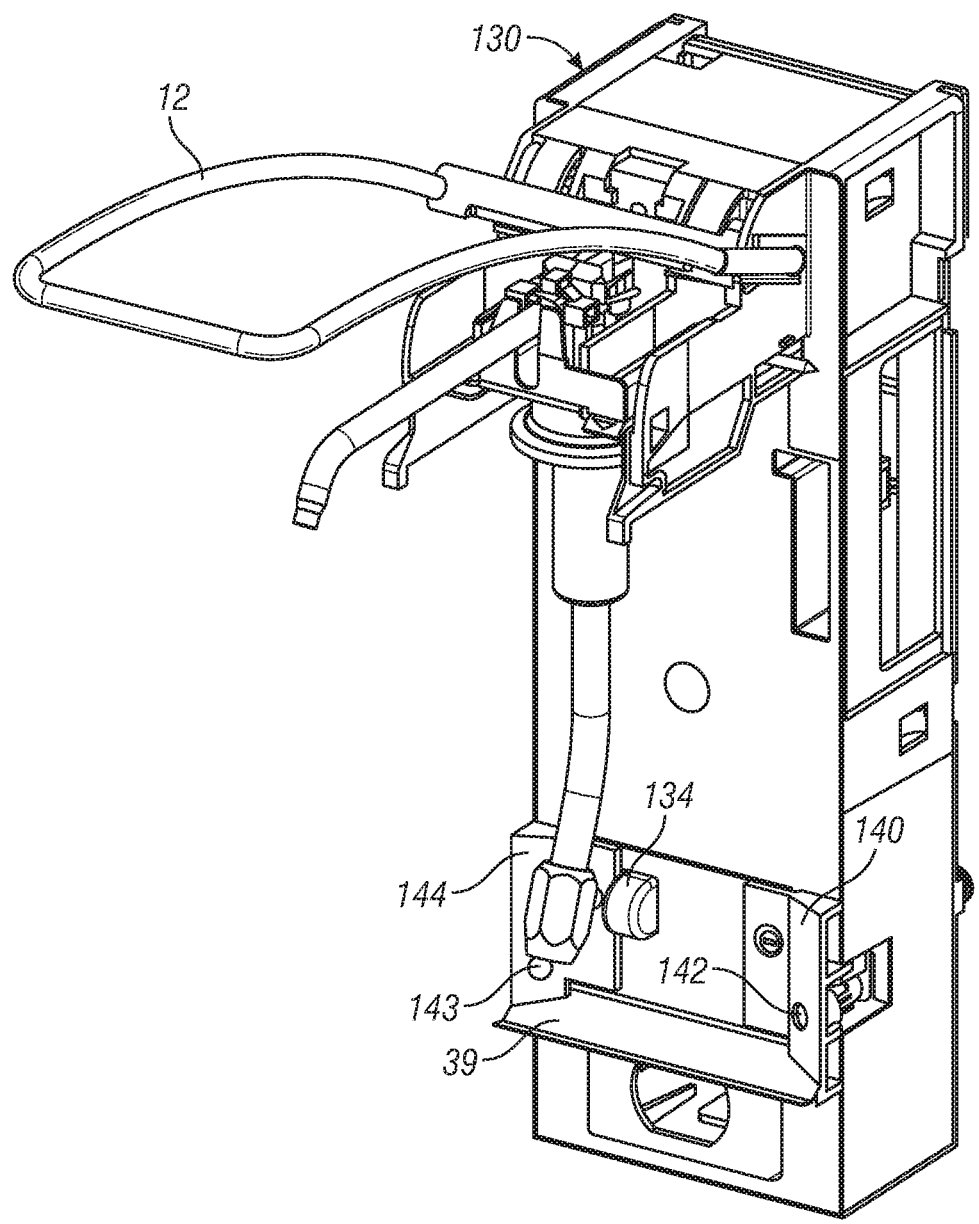
FIG. 15 is a front perspective view of an interior chassis of the dispenser of FIG. 13.
Figure 16:
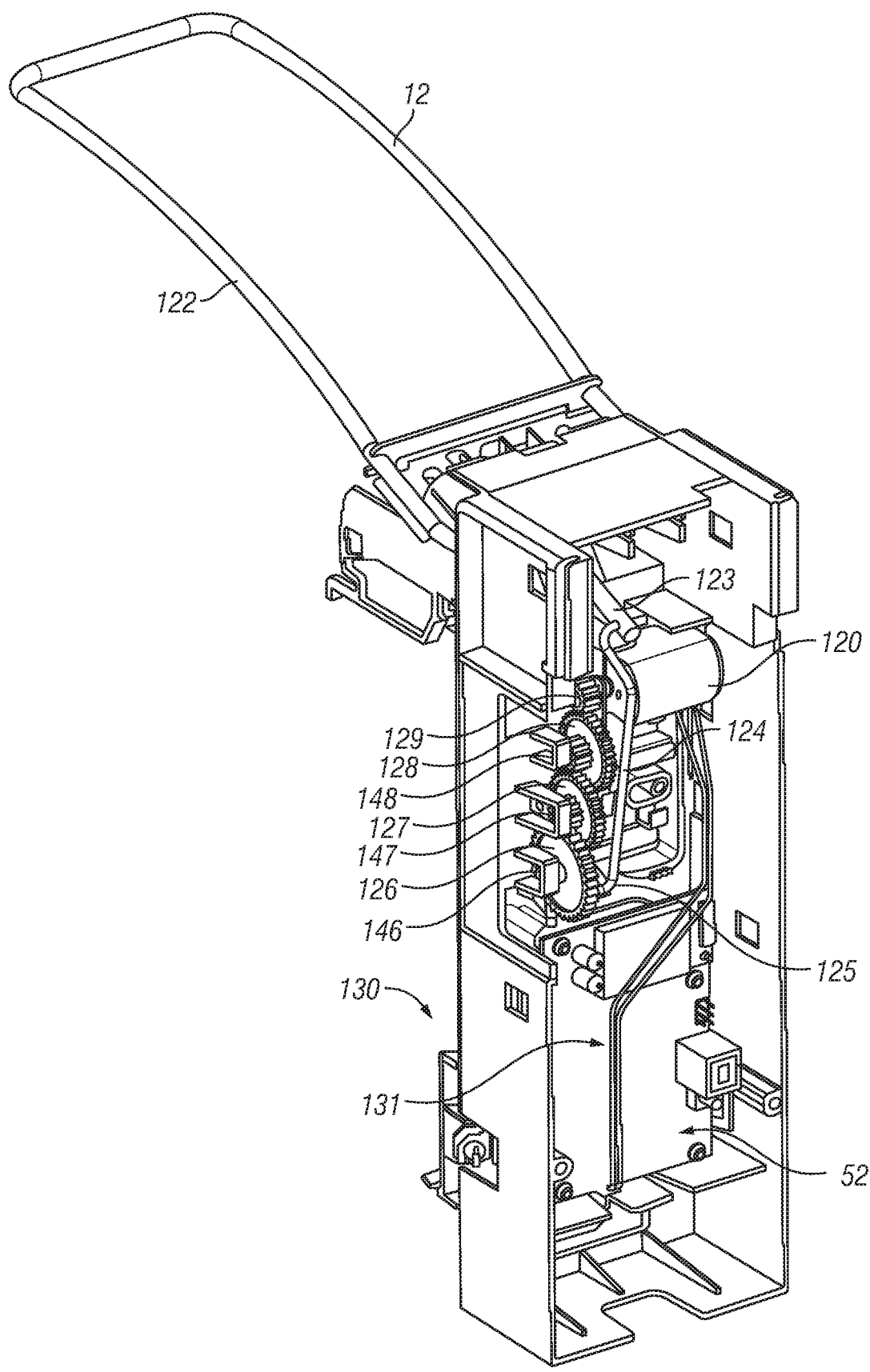
FIG. 16 is a rear perspective view of the chassis of FIG. 15 with its back plate and selected other elements removed to facilitate understanding.

In discussion of the second embodiment of FIGS. 13 to 17, the same reference numerals as used in FIGS. 1 to 12 are used to refer to similar elements. The dispenser 10 of the second embodiment is substantially the same as the dispenser 10 of the first embodiment with the exception that a number of additional features are added. The dispenser has a chassis 130 within its housing 16. Most notably, as seen in FIG. 16, the dispenser includes a generator 120 to generate electrical power on a user moving the lever 12. As seen in FIG. 16, the left hand arm 122 of the lever 12 extends rearwardly for pivotal connection near a rear end 123 of the arm 122 to the upper end of a rigid link arm 124. A lower end 125 of the link arm 124 is pivotally connected to a first drive gear 126 by being engaged journalled for rotation in an opening extending axially through the first drive gear 126 at a radial location spaced from the axis about which the first drive gear 126 rotates. The first drive gear 126 is connected by a series of gears 127 and 128 which are linked to a gear axle 129 on the generator 120. While not shown in FIGS. 13 to 17, the handle 12 is preferably biased to a raised upper position by springs such as the springs 26 shown in FIG. 4. On movement of the handle 12 downwardly by a user to dispense fluid against the bias of the springs, the link arm 124 rotates the first gear 126 and hence rotates the gears of the gear train to rotate the generator to generate power. After a user has moved the lever 12 to a lower position in which the springs are compressed, on release of the lever 12 by the user, the lever will return to the raised position under the bias of the springs. In one preferred gearing arrangement, during movement of the lever 12 from the lower position to the upper position as under the influence of springs, the first gear is preferably mechanically disconnected from the generator 120 as by a one way clutch arrangement. In a second preferred gearing arrangement during movement of the lever 12 from the lower position to the upper position under the influence of springs, a mechanical gearing connection is maintained between the first gear and the generator 120 to harvest electrical energy from the movement of the lever 12. Such gearing arrangements are known to persons skilled in the art.

Figure 13:
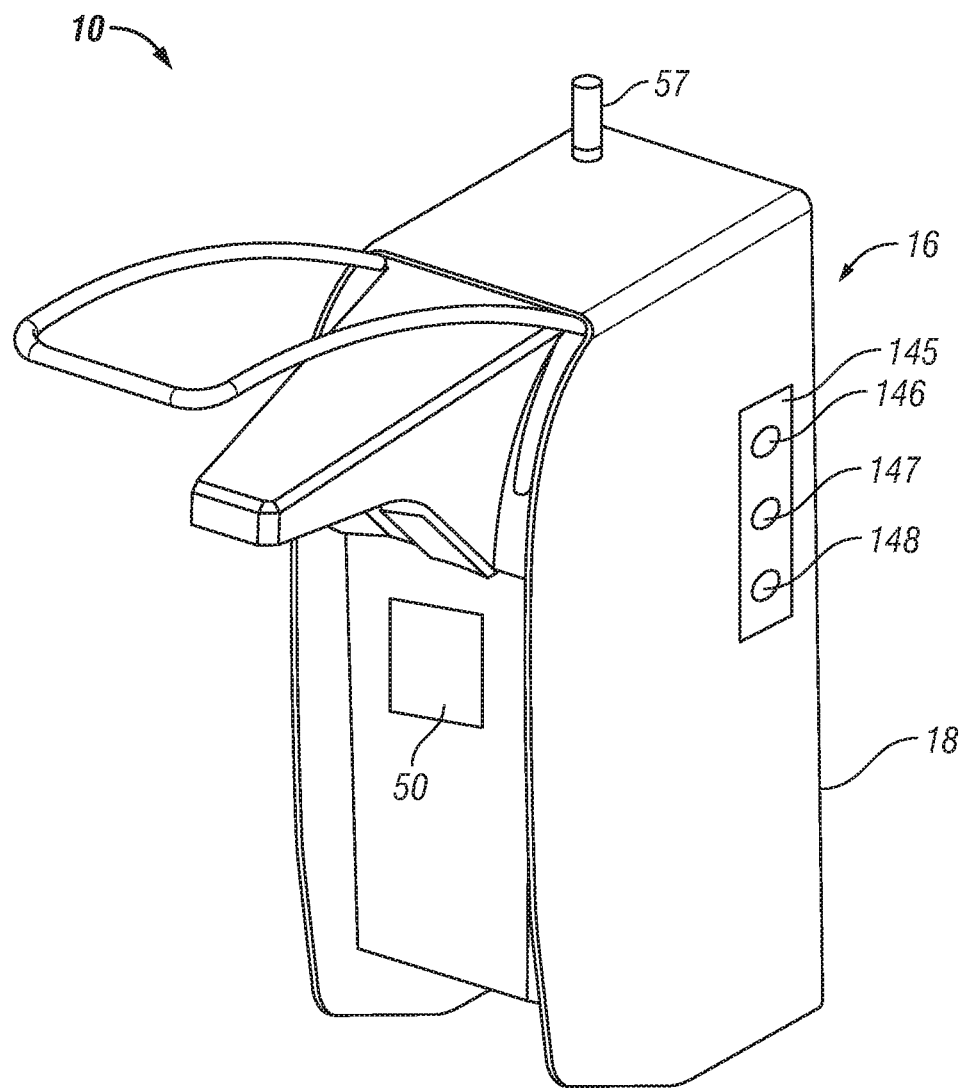
FIG. 13 is a front perspective view of a soap dispenser in accordance with a second embodiment of the invention with a bottle attached thereto.

In the embodiment of FIGS. 13 to 16, the control module 52 as seen in FIG. 16 as secured to the rear of the chassis 130. Electrical wires 131 deliver electrical power from the generator 120 to the control module 52. Referring to FIG. 15, a bottle sensor 134 is provided. The bottle sensor 134 is schematically illustrated in a schematic cross-sectional plan view in FIG. 17 as biased forwardly by a spring member 136 to an extended position shown in FIG. 15. On a bottle 35 being coupled to the dispenser 10, a rear wall of the bottle 35 engages the bottle sensor 134 and urges the bottle sensor 134 rearwardly against the bias of the spring member 136. The forward and rearward movement of the bottle sensor 136 opens and closes an electrical switch 137 providing a signal to the control module 52 indicative of whether or not a bottle 35 is coupled to the dispenser 10.

As also seen in FIG. 15, on the front of the chassis 130 above the support ledge 39 on either side, there are provided angled surfaces 140 and 141. On the surface 140 an infrared emitter 142 is provided and on the surface 141, an infrared sensor 143 is provided. This emitter 142 and sensor 143 provide a level sensing mechanism which is adapted to sense the level of fluid in the bottle 35 and to provide a signal to the control module 52 indicative of whether or not the level of fluid in the bottle is above or below the height of the sensor 143.

As seen in FIGS. 13 and 14, a transparent window 145 is provided through the side wall 18 of the housing 16. Disposed on the chassis 130 inside this window 145 are a series of LED lights 146, 147 and 148 as best seen in FIG. 16. Each light is preferably capable if emitting light of different colors, preferably green, or yellow or red, and capable of being illuminated continuously or to flash intermittently. The lamps are preferably controlled by the control module 52 to provide visual signals to users as to the condition of the dispenser. One of the lights can, for example, emit, green, yellow or red light as, for example, to indicate that a level of contamination sensed by the sensor is, respectively acceptable, moderate or unacceptable. The lamps can also provide signals indicating that the bottle is empty of fluid or that there is some other malfunction or that the dispenser is operational.

In the second embodiment of FIGS. 13 to 16, in addition to the lights which indicate the status of the dispenser, a speaker indicated as 170 may be provided connected to the control module and adapted to be activated so as to provide, for example, spoken signals or direction to a user of the dispenser or a person replacing the bottle and/or sensor and/or warnings at different levels depending upon the status of the dispenser and the level of contaminant sensed.

FIG. 13 illustrates a bottle 35 as coupled to the dispenser which bottle is substantially of the type illustrated in FIG. 9, that is, with a sensor 50 carried on the front face of the bottle and coupled to the control module 52 either in a wired manner as illustrated in FIG. 4 or 12 or an unwired manner as in FIG. 9.

A dispenser in accordance with the present invention in the preferred embodiments illustrated comprises a manually operated dispenser. However, dispensers for use in accordance with the present invention are not so limited. A dispenser need not be manually activated. A dispenser may include an electronically activated dispenser in which, for example, dispensing of fluid is activated automatically by a sensor sensing the presence of a user's hand underneath a dispensing outlet. Such automatic dispensers which are preferably touchless include a control module for their operation and, in accordance with the present invention, a sensor would be provided on the dispenser to sense contaminants. The sensor may preferably communicate in a wired or wireless manner with the control module in the automatic dispenser or, as described alternatively, communicate directly with a wireless hub.

Figure 18:
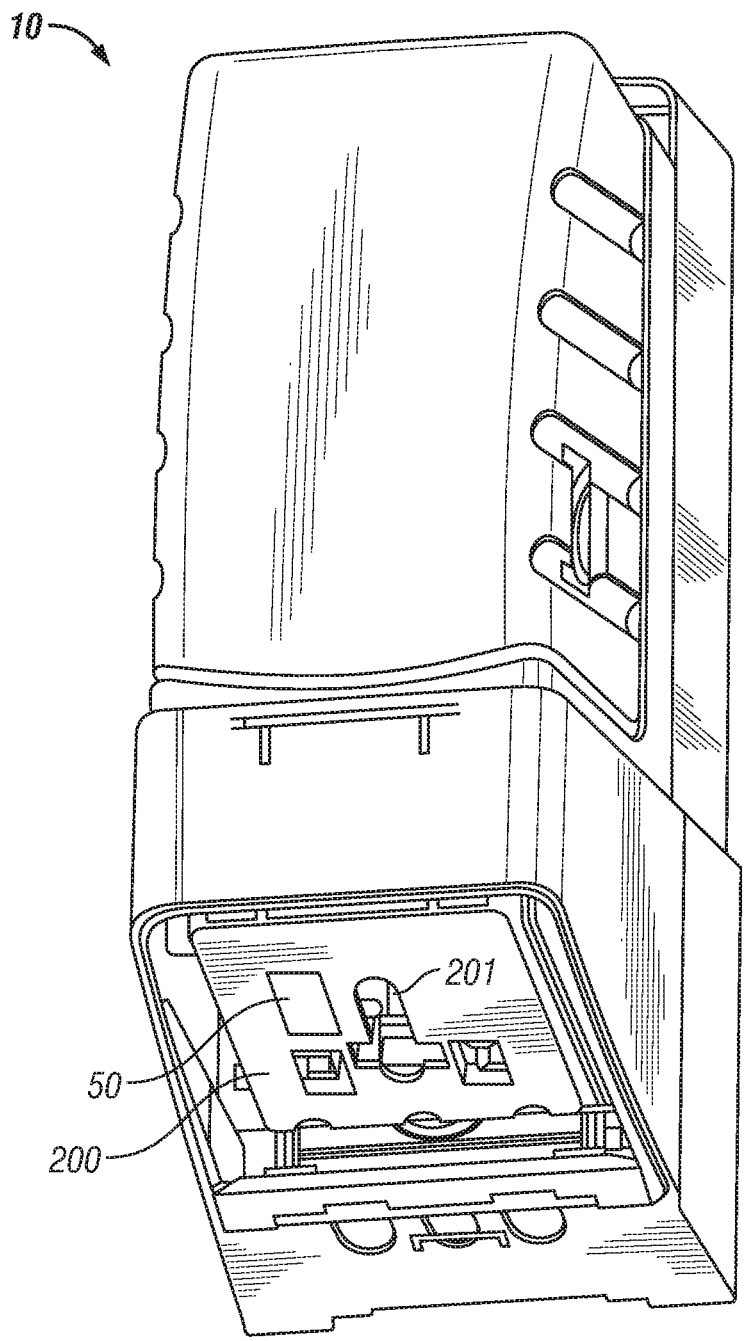
FIG. 18 is a front perspective view of a soap dispenser in accordance with a third embodiment of the invention.

Reference is made to FIG. 18 which illustrates a touchless dispenser of the type disclosed in U.S. Pat. No. 7,980,421 to Ophardt et al. issued Jul. 19, 2011, the disclosure of which is incorporated herein by reference, and which dispenser 10 has been modified merely to show a contaminant sensor 50 provided on a downwardly directed surface 200 proximate the discharge outlet 201 for fluid from the dispenser 10. Of course, additional contaminant sensors 50 may be provided at different locations on such a dispenser. In a known manner, hand sensors 203 sense a person's hand below the nozzle 13 and actuate a pump (not shown) to discharge fluid from a fluid reservoir 35.

Figure 17:
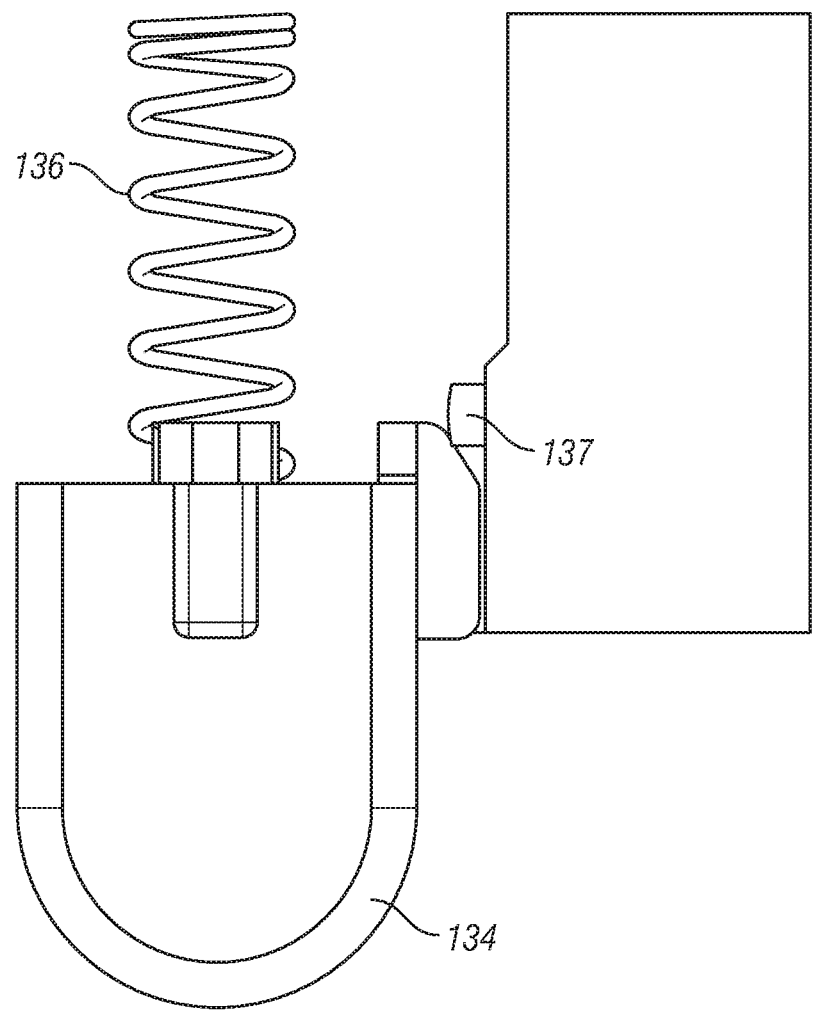
FIG. 17 is a schematic partial cross sectional plan view through the bottle sensor in FIG. 15.

One preferred sensor for use in accordance with the present invention is a sensor which has a relatively limited lifetime over which the sensor is effective to sense a contaminant as, for example, with the sensor operative such that once a certain quantity of contaminants come to engage the surface of the sensor, the sensor is no longer operative to indicate changes in level of contamination. A preferred sensor 50 for use in the present invention may have a contaminant sensing mechanism 73 as seem in FIG. 19 which comprises a circuit board 159 plurality of individual sensing areas or elements 160. Each individual sensing element 160 is each adapted to be independently electrically connected to the control module 52 via wires 165 and activated. The control module 52 is schematically shown in FIG. 17 in dashed lines. Each sensing element 160 has a separate release member 80 covering it and preventing engagement of contaminants with the sensing element 160 until the release member 80 is removed. In FIG. 17, an electrical heating element is provided underneath each sensing element 160 on the circuit board 159 with the electrical heating element electrically connected to the control module 52. For ease of illustration but one such electrical heating element 162 is shown in dashed lines with its connecting wires shown as 163. Each release member 80 is a sheet of material which is volatile when heated above room temperature. The control module 52 is capable of providing electrical energy to each heating element 162 to heat the release member 80 and have it sublimate and dissipate so that the underlying sensing element 160 is initially activated to receive contaminants. The control module 52 is to heat the heating element 162 for each of the individual sensing elements 160 at times when desired, preferably activating different of the individual sensing elements 160 at different desired times as, for example, in sequence over a period of time.

Other systems for time delayed and time staggered activation of the individual sensing elements 160 include the use of volatile release members 80 which at room temperature sublimate with time and which are provided to be of different initial thicknesses over different of the individual sensing elements 160, or of materials which dissipate at different rates over of the individual sensing elements, so as to provide for different of the individual sensing elements become open to receive contaminants at different times. Preferably, with the control module 52 can determine the time when each of the individual sensing elements 160 are initially activated.

The individual sensing elements 160 can be relatively small, for example, of dimensions to provide a surface area of less than 1 square cm, more preferably less than 0.5 square cm, which assist in also providing for each sensor 50 to also be relatively small. Preferred individual sensing elements 160 and other portions of a sensor 50 may be printed by various techniques such as to become OLED circuits as printed on a thin film such as on PET film. Such small sized individual sensing elements 160 and sensors 50 may be adapted as, for example, for location on relatively small sized areas as on the lever 12 or on the nozzle 13 shown in the embodiments of FIGS. 1 and 13 which may, for example, comprise tubular members of a diameter in the range of not greater than about ¼ inch.

A dispenser in accordance with a second embodiment of the invention is capable of providing information as to the level of contaminant sensed by the dispenser over a period of time. The dispenser also has the capability for providing information as to the time when a bottle is replaced, the time when the bottle is empty and the number of activations of the pump. The number of activations of the pump can readily be sensed by sensing when power is provided from the generator 120 to the control module 52. As a result of this information, the level of activity of the dispenser can be known. The level of activity of the dispenser has a correlation to the number of times persons activate the dispenser to dispense fluid. The number of activations of a dispenser over time can be another factor to be used in comparing the dispenser and level of contaminants in any dispenser or group of dispensers within an array to any other dispenser or group of dispensers within the array.

Information can be provided to a central server as to a specific location of any dispenser within a facility. Historical information about any dispensers at that same or proximate location including information about contaminant levels and activation levels can be useful in determining thresholds for comparing contamination levels of any particular dispenser or group of dispensers.

Of contaminants which may be adapted to be sensed by the sensors 50 on the dispensers 10, some contaminants may be airborne and other contaminants may be carried by persons as on their hands. The nature of the contaminant to be sensed can be a factor in determining where to locate the sensor on a dispenser. The nature of the contaminant to be sensed can also have a determination as to whether or not the number of activations is a significant factor in assessing levels of a contaminant with time at any particular dispenser. Preferably, contaminants which are carried as, for example, on a user's hand will be placed on a dispenser at a location where the sensor is likely to be contacted by a user's hand. Dispensers which are adapted to sense airborne contaminants may be located at different locations on the dispenser remote from possible contact by a user.

Figure 20:
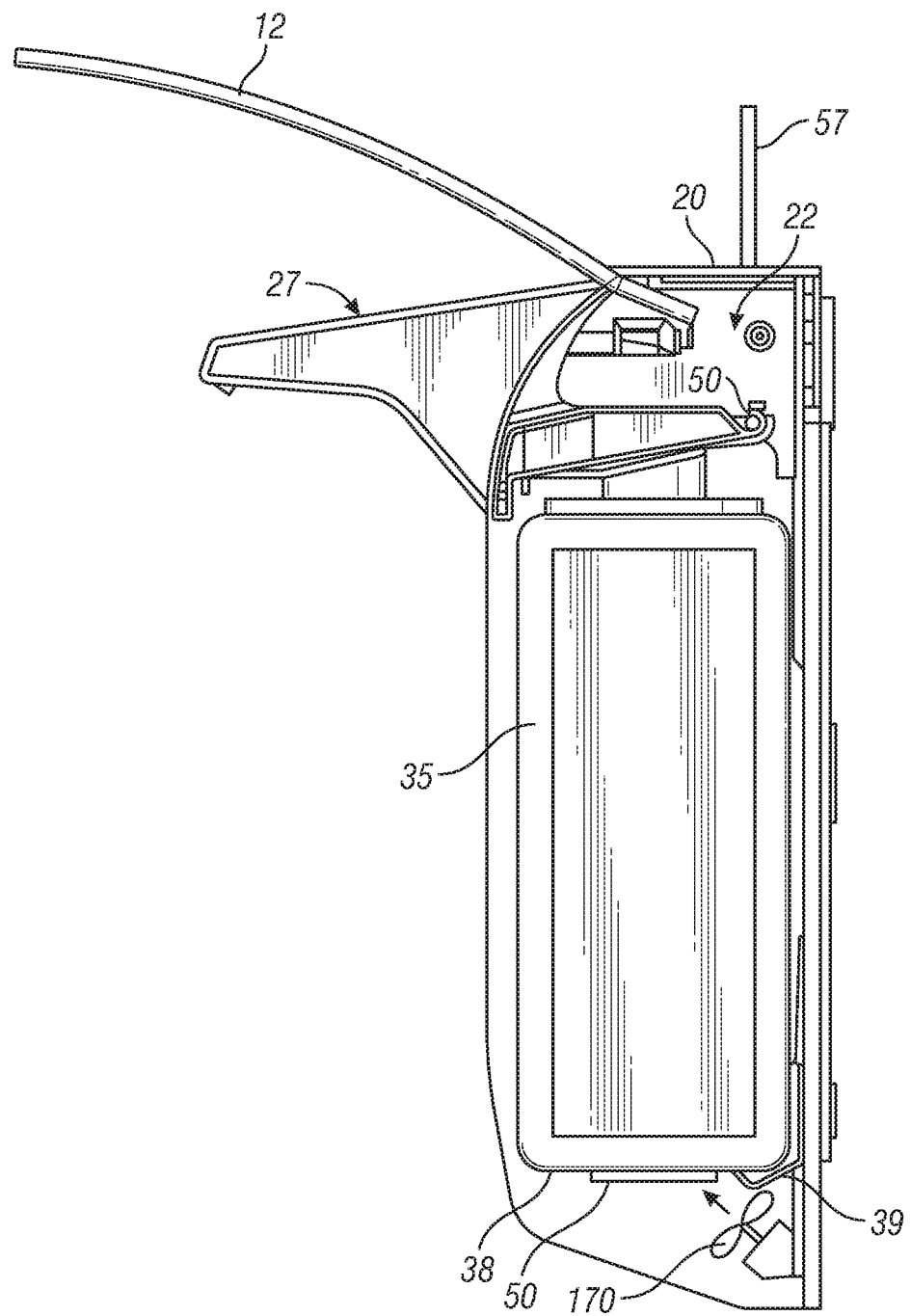
FIG. 20 is a cross section similar to FIG. 5 but showing a fan to blow air over a sensor provided on the bottom of the bottle.

Reference is made to FIG. 20 which shows an embodiment of a soap dispenser 10 of the present invention similar to that shown in FIG. 3 but in which a sensor 50 is provided on the bottom 38 of a bottle 35 so as to be located forwardly from the support ledge 39. An air fan 170 is provided to be secured to the back of the dispenser 10 underneath the support ledge 39 so as to blow air onto the sensor 50. The fan 170 is electrically powered and controlled by the control module 52 (not shown). The fan 170 may direct air onto the sensor 50 continuously or more preferably periodically for short intervals from time to time during the useful life of the sensor 50. In this manner, in a controlled manner, the sensor 50 may engage with air from about the dispenser 10 and more accurately provide for sensing of airborne contaminants.

As to the particular nature of the contaminants which the sensor 50 may sense, this is not limited. A most preferred application is the use of the sensors as in hospitals, food facilities, restaurants and the like to sense biologic contaminants such as bacteria, micro-organisms, viruses, fungi, molds, spores and signalling molecules or other products or by-products of bacterial, micro-organisms, fungi and molds. However, the sensors may also be adapted to sense other contaminants such as the relative levels of carbon monoxide, carbon dioxide, oxone, oxygen, nitrogen, natural gas and other gases. The sensors may also sense for smoke as by sensing carbon particles that may be airborne residue of a fire. The particular nature of the contaminants to be sensed is not limited. The sensors may also be used to sense other variables such as temperature, humidity, atmospheric pressure, and light and noise levels.

Figure 21:
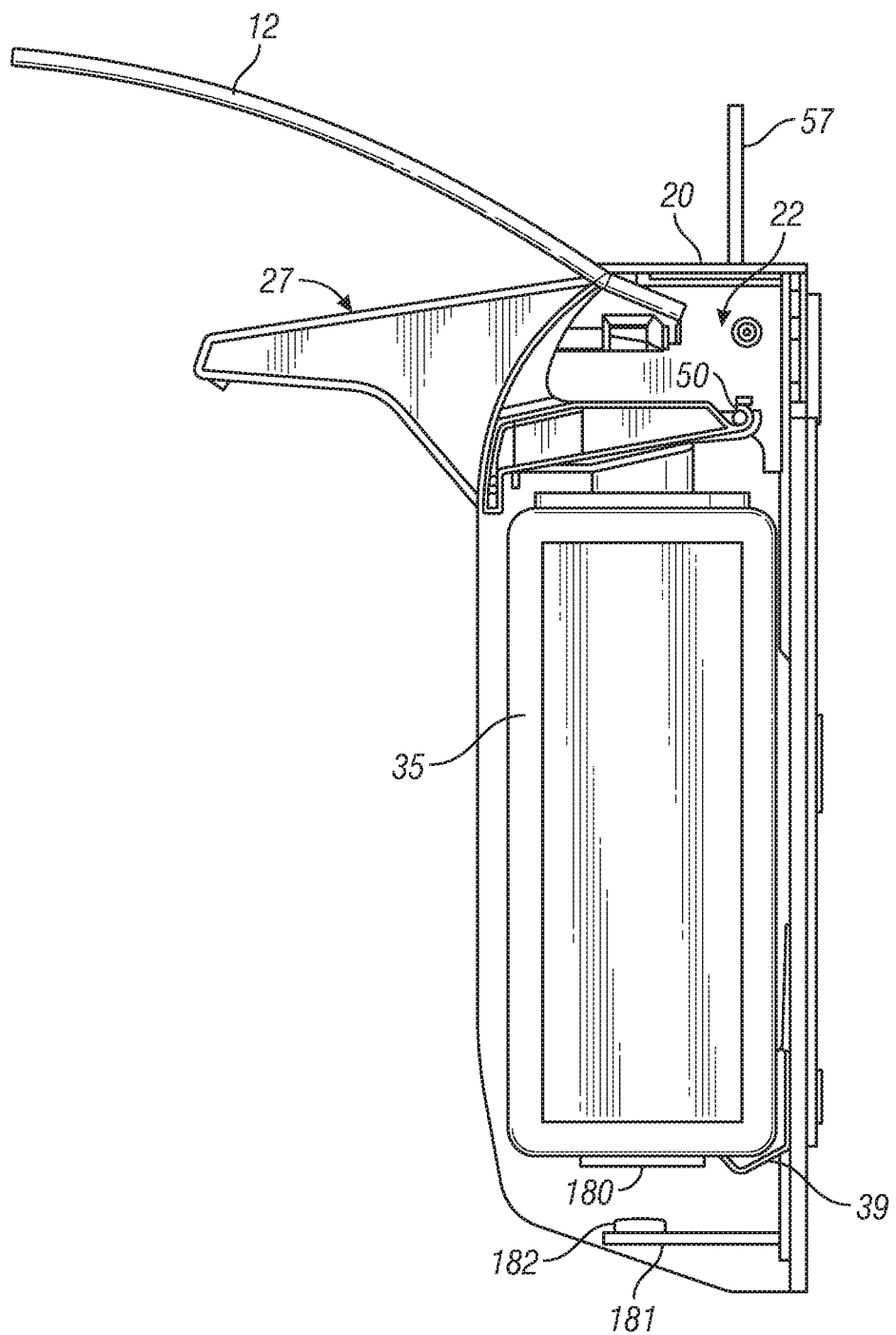
FIG. 21 is a schematic partial front and bottom perspective view of a fourth embodiment of a dispenser in accordance with the present invention showing an indirect optical color sensor.

The particular nature of the sensors to be used is not limited. The sensor may be a direct sensor or an indirect sensor. A direct sensor would provide a signal as to levels of contamination is preferred. Preferred direct sensors are electronic with a sensor identifying the presence of a contaminant on its surface and providing for an electronic signal. Such sensors are well known and include biosensors as applied to biochips. The biosensor is a device that includes a biological recognition system, often called a bioreceptor, and a transducer. The interaction of an analyte with the biosensor is designed to produce an effect measured by the transducer, which converts the information into a measurable effect, such as an electrical signal. The biosensor typically includes associated electronics or signal processors that are primarily responsible for the display of results in a user friendly manner. Biosensors that include transducers based on integrated circuit microchips are often referred to as biochips. A biochip typically includes one or more in biosensors that can be individually monitored. Biosensors and biochips can be classified either by their bioreceptor or their transducer type. A bioreceptor typically is a sensitive biological element, a biologically derived material or a biomic material such as a biological molecular species or a living system or biologic material, for example tissue, micro-organism, organelles, cell receptors, enzymes, antibodies, nucleic acids, etc, that utilizes a biochemical mechanism for recognition. The sampling component of a biosensor can contain a bio-sensitive layer. The bioreceptors are the key to specificity for biosensors as they are responsible for the analyte of interest to the sensor for measurement. Biosensors can take many forms, however, include five major categories: antibody/antigen, enzymes, nucleic acids/DNa, cellular structures/cells and biomimetic. Biosensors can also be classified based upon the transduction method. Transduction can be accomplished by a great many methods. Most forms of transduction can be categorized into one of the following classes; optical detection methods, electrochemical detection methods and mass deduction methods. Each of these three classes contain many different subclasses. An indirect sensor may also be used. An example of an indirect sensor is shown in FIG. 21 which is similar to FIG. 3. FIG. 21 illustrates in a side view similar to FIG. 3, a component of sensor 50 in the form of an indicator sheet 180 removably secured to the bottom 38 of the bottle 35. The indicator sheet 180 is a sheet material whose color changes as a contaminant comes to engage the sheet. The sheet 180 may, for example, be of an initial colour such as white and will change successfully from white to another colour such as, for example, a deep red when contaminant has come into contact with the sheet. The sheet 180 preferably changes gradually in colour from white to red passing, for example, through white, red or pink colours before it reaches a deep red colour. The extent to which the colour red is displayed by the sheet 180 is indicative of the level of contaminants that have cumulatively engaged the sheet 180.

Mounted on the dispenser 10, as carried by a flange 181 secured to the back of the dispenser housing 16 below the support ledge 39, there is provided an optical sensing element 182 directed to be in opposition to the sheet 180. The optical sensing element 182 is an electronic element which has a capability of sensing the colour of the sheet. The optical sensing element 182 is electrically controlled and connected to the control module 52 not shown. The optical sensing element 182 monitors the colour of the sheet and provides suitable signals indicating the colour of the sheet and thus a representation of the level of contaminants sensed. The indicator sheet 180 may have a lifetime until the cumulative contaminants engaged on it turn its colour to a deep red. The indicator sheet may be provided at various locations on the dispenser 10 or on the bottle 35 and can be removed and replaced.

Figure 19:
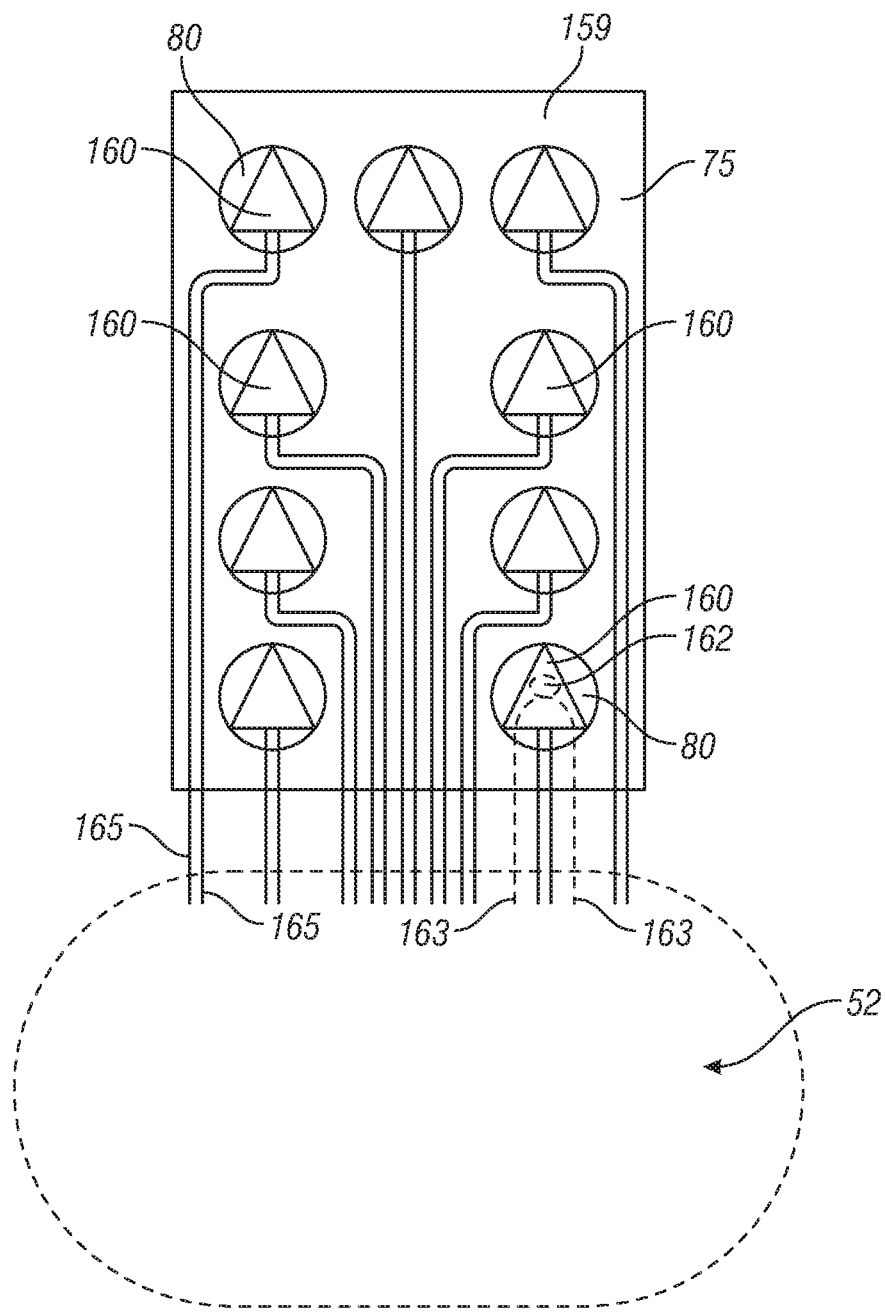
FIG. 19 is a schematic plan view of a sensing mechanism for a sensor carrying a plurality of individual sensing elements and schematically shown as coupled to a control module.

If it is desired to protect any sensor, whether direct or indirect, from damage by contact with a person using the dispenser or fluids dispensed, the sensor can be provided at a protected location as, for example, in the middle of a rear wall of the bottle 35 and, if advantageous, have an air fan 170, for example, similar to that shown in FIG. 19, direct air flow over the sensor 50 towards providing air from the environment in controlled contact with the sensor.

A variety of contaminant sensors may be used in accordance with the present invention without limitation including, magnetoelastic, microelectromechanical microphysiometer, nanowire, waveguide, liquid crystal, distributed dust or DNA bridge sensors. A description of each is provided in this paragraph; however, more detailed information of each is readily available in the open literature. A magnetoelastic sensor monitors a change in resonance of a tuned magnetoelastic strip which has been coated with an antibody of the analyte to be detected. The antibodies on the surface of the magnetoelastic strip bond with the analyte when present, changing the mass, and consequently, the resonant frequency of the element which change in mass can be detected to issue a signal. To detect multiple toxins, multiple individual strips may be coated with respective antibodies, ganged together and monitored by a common computer chip for issuing signals. A microelectromechanical sensor monitors changes in the resonance of a spring-mass with a small cantilever beam coated with an antibody of the analyte to be detected to capture a small mass of analyte to effect a change in mass, and, consequently, the resonant frequency of the cantilever beam. A microphysiometer sensor employs live human cells that have been adapted to react quickly to biological agents in the environment. These cells are disposed atop sensors that detect abnormalities in cell structure. Nanowire or DNA bridge sensors employ strings of DNA disposed in or completing an electrical circuit which changes conductivity or resistance as receptors in the DNA molecule accept or combine with other DNA molecules. These DNA strings can be adapted to receive or combine with analyte DNA to detect and issue an alert signal. Waveguide sensors employ a coating of antibodies which are disposed on a sensor surface and selected to target specific analytes such as bacteria cells. When the antibodies come into contact with these bacteria, the antibodies attack and destroy the bacteria and a light source is used to illuminate the changes. As the antibodies destroy the bacteria, the sensor surface detects the changes allowing the bacteria to be identified. Liquid crystal sensors employ cell membranes disposed atop rod-shaped liquid crystals to detect analytes. For example, lipids are attached to the liquid crystals, which lay perpendicular to the surface and appear dark. When the sensor is exposed to a protein that binds to the lipids, the liquid crystal molecules rapidly respond by switching to a planar orientation. As a result, the crystals transmit polarized light and appear bright. The change in illumination can be detected to issue an alert signal. Distributed dust sensors employ micrometer size particles which change color in the presence of contaminate. For example each particle can exhibit different colors depending upon its orientation such that when attaching to a particular contaminate, the particles collectively yield a characteristic optical signature. The change in optical signature can be detected to issue a signal. Immunoassay sensors employ reactive materials which change color or contrast in the presence of an analyte. A sensor can includes a white absorptive stick coated with the reactive material which, upon contaminant exposure, effects a color change.

The contaminant sensor provides an electrical output or switch closure, or changes in color, contrast or other physical characteristics can be converted to an electrical output/switch closure by conventional photoelectric or optical devices.

Each dispenser as illustrated in the embodiments of FIG. 1, FIG. 13 and FIG. 18 are adapted for dispensing fluids as, for example, on the hand of a user. The particular nature of the fluid which may be dispensed is not limited. The fluid typically is dispensed as a liquid or as a foam. The invention is applicable to fluid dispensers of virtually any manner or configuration in which a user has some interaction with the dispenser and there is an opportunity for interaction between the user and the dispenser or the environment about the dispenser. As to the particular nature of the fluid to be dispensed, these may include soaps such as aqueous based soaps and other cleaning fluids such as alcohol based cleaners and disinfectants. The units may be used in various different areas in a facility such as in common public areas in a hospital, on patient wards with or without restricted access and in areas which must be kept highly sanitized such as in operating rooms and rooms for preparation and cleaning before entering operating rooms.

While FIGS. 1, 13 and 21 illustrate but three forms of fluid dispensers, many fluid dispensers fall within the scope of the present invention including foot washers as are known for dispensing fluid onto the foot of a user as, for example, by spraying a fluid onto a foot of a user on activation of a user to dispense the fluid by the foot being sprayed.

The preferred dispenser as shown in FIGS. 1 and 13 are adapted for engagement by a user's hand to activate the dispensing of fluid. Dispensers are known which are adapted for activation by engagement by other parts of a user such as a user's elbow or foot. Some fluid dispensers are activated by a user pushing a button to electrically operate a pump. All such dispensers are included within the scope of the present invention.

Many paper dispensers are known as for use in washrooms, health care facilities and the like in which a user activates the dispenser so as to dispense paper products typically in rolls or sheets to the user. Such paper dispensers include dispensers which may have a lever handle for engagement by a user, for example, to rotate a roll of paper and provide a portion of the paper accessible for a user to tear off. Other paper dispensers are automatic and touchless and sense the presence of a user, hence, dispensing a portion of the paper as for drying a user's hands. Other paper dispensers dispense toilet paper as found beside or near a toilet and typically require a user to manually engage the end of the paper and draw the paper from a paper dispenser whether the paper may be in the form of a roll or the form in sheets. In each of these dispensers, there is an opportunity for a user to engage portions of the dispenser and there are surfaces on the dispenser where contamination may occur. With each of these paper dispensers as is the case with fluid dispensers, the paper is a replaceable personal product and needs to be replaced periodically. In the case of a paper dispenser dispensing papers on rolls, the roll of paper comprises a replaceable cartridge which must be replaced from time to time. As is the case with a fluid dispenser, at the time of replacing a replaceable cartridge in a paper dispenser, a removable and replaceable sensor may be provided with the paper cartridge such that each time a replaceable paper cartridge is provided a new sensor is provided for the paper dispenser. As with the fluid dispensers, the sensor provided with the cartridge is adapted to be located open to an environment in which contaminants may be desired to be sensed as by maintaining this position on the cartridge while being gathered to the cartridge for coupling to the dispenser or being removable from the cartridge for coupling to the dispenser.

The fluid dispensers in accordance with the present invention are more preferably fluid dispensers for dispensing cleaning and disinfecting solutions and, more particularly, those adapted for cleaning a user's hands. Similarly, a paper towel dispenser to which the invention most directly relates are those adapted to be provided in an environment where a person's hands are desired or expected to have been cleaned as, for example, notably in washrooms and in health care and food preparatory facilities.

Figure 22:
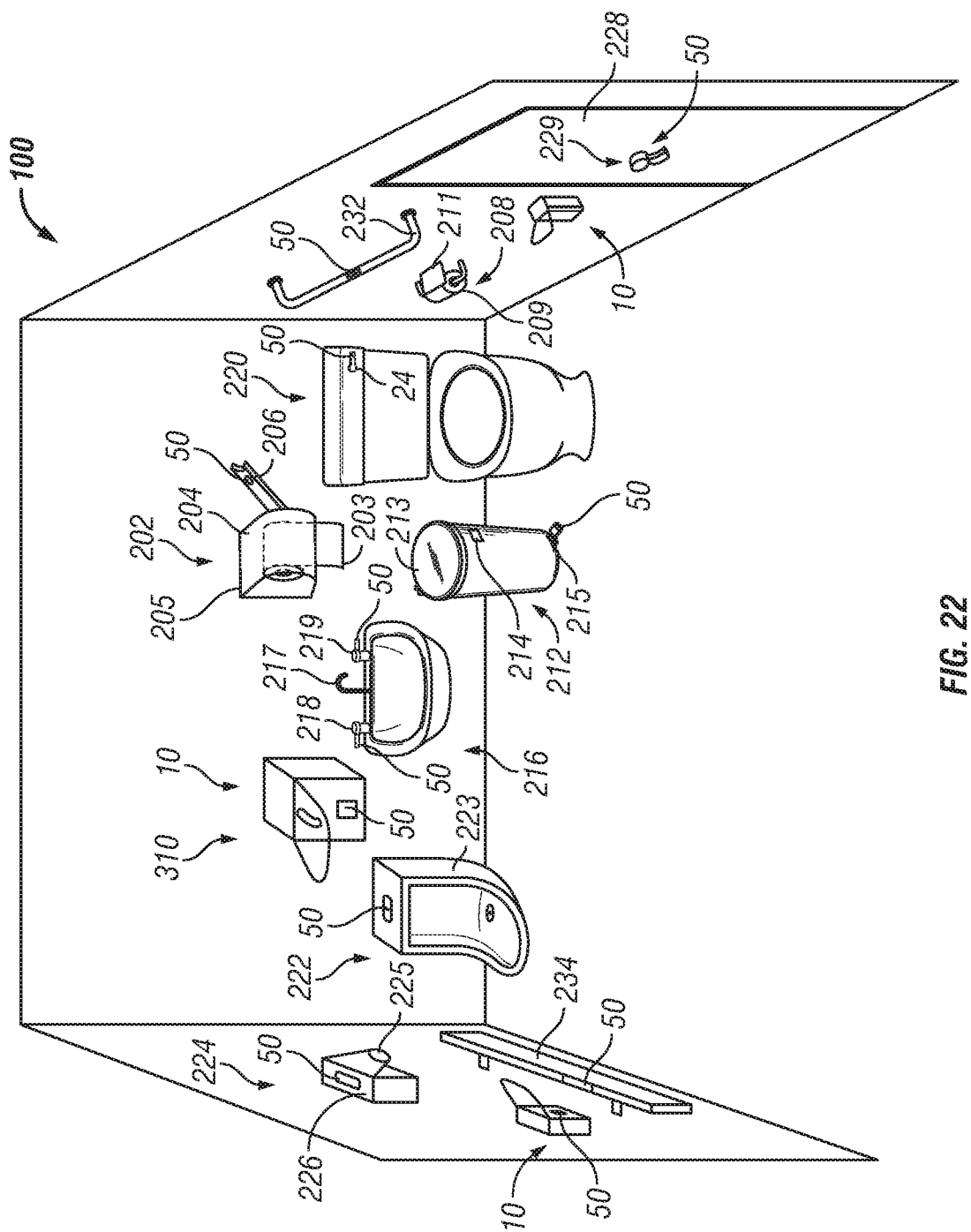
FIG. 22 is a schematic collage of a plurality of elements which may be found in a facility and which may be monitored in accordance with methods of the present invention.

Reference is made to FIG. 22 which illustrates a collage of elements which may be found within the facility schematically illustrated as 100. These elements include the following: (a) dispensers 10 for dispensing fluid onto a user's hands, (b) a paper towel dispenser 202 for dispensing paper towels 203 from a horizontally disposed roll of paper schematically illustrated in dashed lines as 204 within a closed housing 205 carrying a lever arm 206 for operation to dispenser the paper 203, (c) a toilet paper dispenser 208 having a replaceable roll of paper 209 mounted as for rotation at least partially covered by a housing 211; (d) a foot spray dispenser 212 typically mounted approximate to a floor and having a housing 213 carrying a replaceable reservoir therein and from which fluid is adapted to be dispensed as in a spray nozzle 214 by a user engaging a lever 215 with his foot, (e) a sink 216 having a faucet 217 for dispensing of fluid and activated by two levered handles 218 and 219, (f) a toilet 220 having a handle 221 which can be manually engaged for flushing, (g) a urinal 222 having a push button 223 for engagement by a user for flushing, (h) a wall mounted air blowing hand dryer 224 for dispensing of a flow of air out of an enlarged nozzle tube 225 and adapted, for example, for activation by a push button 226, (i) an access door 228 for providing access to an area in a building or to a bathroom stall and adapted to be opened and closed by manual engagement of a door handle 229, (j) a grab bar 232 adapted to be engaged to a wall to provide for assistance in a user in standing or sitting as adjacent to the toilet shown, and (k) a handrail 234 adapted to be mounted adjacent a wall for engagement by a user for guiding a user in movement along a wall and to assist in supporting a user by engagement by a user's hand, which handrail may also be adapted for placement along or beside one or more stairs. Each of these elements carries a sensor 50 in accordance with the present invention.

Each of the dispenser 10, the paper towel dispenser 202, the toilet paper dispenser 208 and the foot spray dispenser 212 dispense a personal product which product needs to be replaced from time to time and typically is replaceable as in the form of a reservoir or cartridge. In accordance with the present invention, each of the fluid dispenser, paper towel dispenser, toilet paper dispenser and foot spray dispenser carry a contaminant sensor 50 in accordance with the present invention preferably which is provided with and replaced with the replaceable reservoir or cartridge. In accordance with the present invention, wireless contaminant sensors 50 are provided on other of these elements in the facility 100 facility, and preferably on any other elements which are reasonably to be expected to be engaged by users, preferably where they may be expected to be engaged users. Thus sensors 50 schematically indicated by arrows to be provided on each of the handles 218 and 219 for the sink 216, the toilet handle 221, the urinal push button 223, the dryer push button 226, the door handle 229, the grab bar 232 and the handrail 234.

In accordance with a preferred embodiment of the invention, the wireless sensors 50 which are provided on many of the elements may be provided with communication capability for relative limited distance such as, for example, no greater than 4 or 8 or 16 feet, preferably within the same room without capability of passage through walls of the facility. Wireless sensors with such limited range communication may be provided within the range of communication with another element which serves as a message collector. The message collector could be merely a wireless router, however, preferably may comprise another of the elements such as preferably one of the fluid dispensers 10 or one of the paper dispensers. The dispenser 10 which preferably also serves as the message collector preferably has increased communication capabilities for sending information as to the Internet.

Figure 23:
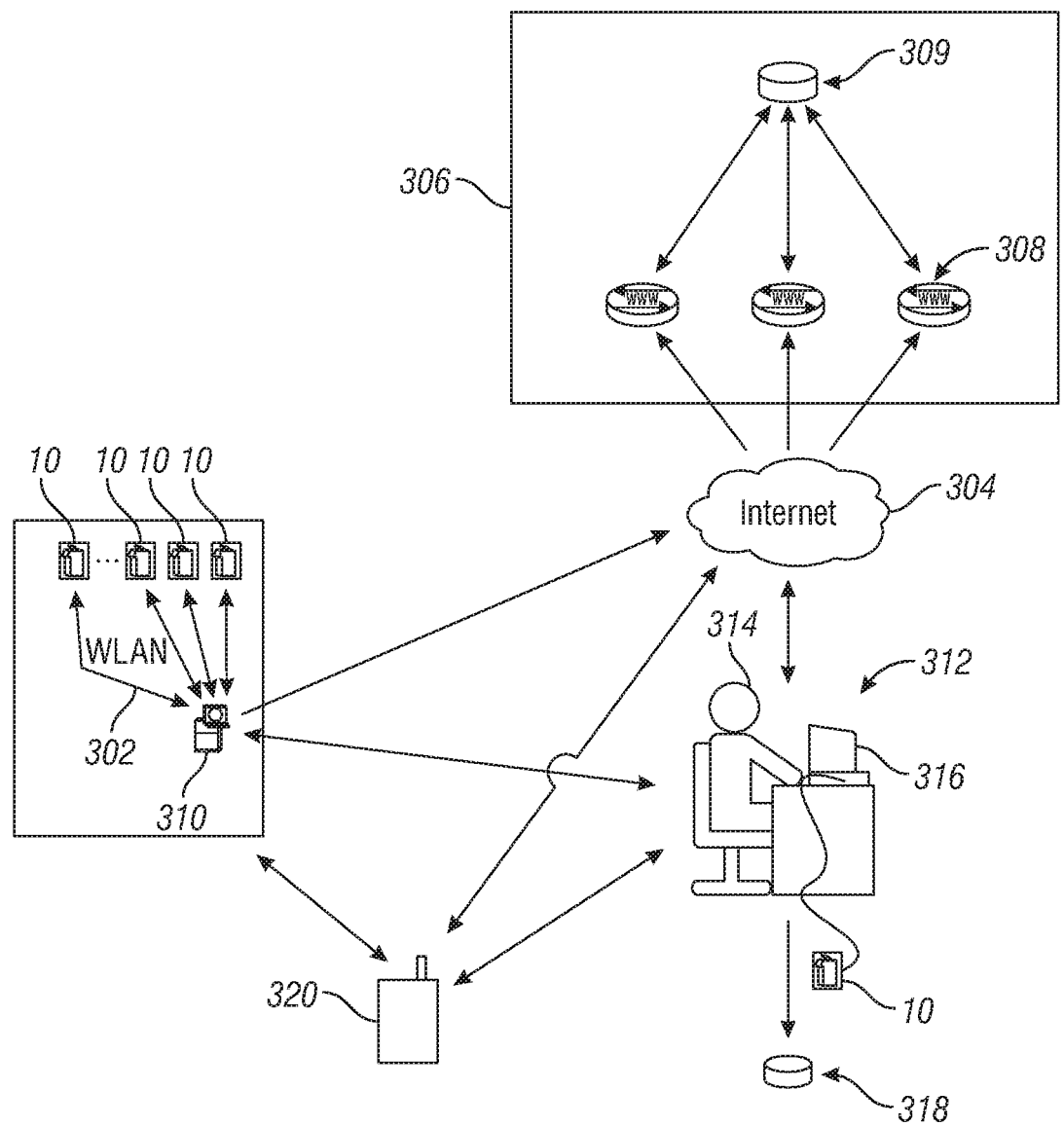
FIG. 23 is a schematic flow diagram showing a second arrangement for monitoring and control of an array of sensor carrying elements in accordance with the present invention.

The particular manner and control of any of the sensors 50 shown on the elements in the collage of FIG. 22 is not limited. One preferred flow diagram of a second arrangement for monitoring and control of the sensor carrying elements of FIG. 22 is illustrated in FIG. 23. FIG. 23 illustrates schematically a plurality of the sensor carrying elements as shown in FIG. 22 adapted to communicate wirelessly via a WLAN 302 to a message collector 310 comprising preferably a particular one of the dispensers 10. This message collecting dispenser 310 is shown as adapted for communication with the Internet 304 as preferably wirelessly. From the Internet 304, information may be passed to a data processing module 306 which typically would comprise a web tier of servers 308 which communicate with a data tier of servers 309. The web tier of servers 308 typically delivers information through web pages, receive user information to be processed, provides web services for multiplexer use and for reporting to the facility manager, generates alerts and notifications and typically is expandable. The data tier server 309 provides a central data storage. A facility manager 312 is shown as schematically illustrated as an individual person 314 at a computer 316. The facility manager 312 is able to communicate with the message collector 310 and, as well, with the data processing web tier 308 and data tier 309 via the Internet 304. The facility manager 312 has the capability, for example, of reviewing reports, managing all master data, and, as well, of registering each of the dispensers 10 and configuring the dispensers 10. As shown in FIG. 23, there is one dispenser 10 shown as connected to the facility manager computer 316 as for initial dispenser configuration via a USB before that dispenser may be placed at its desired location in the facility. FIG. 23 shows the facility manager 312 as also having the capability of communicating with a facility database 318 which may include various information from a facility as, for example, in the case of a hospital, data regarding operations, occupancy, infection incidents and the like.

In accordance with a preferred embodiment of the present invention, the dispensers 10 and other elements which have sensors preferably do not incorporate batteries which require frequent replacement. The inventor of the present application has appreciated that in many facilities such as hospitals there are thousands of such dispensers and avoiding the need for battery replacement can significantly reduce the costs of operation. As such, a preferred arrangement is to provide the dispensers 10 to have a capability of generating through use the energy required for operation of the dispenser. In a configuration as illustrated in FIG. 23, the individual dispensers 10 with limited communication capability may preferably comprise a dispenser 10 of the type illustrated in FIG. 16 which incorporates a generator which generates energy on manual movement of the lever to dispense fluid. The energy necessary to be generated can be merely the energy necessary for relaying from time to time information from that dispenser 10 to the message collector 310. In dispensers 10 with a generator such as shown in FIG. 16 require for their operation some energy to take readings as to maintain a time clock and to store data based on time as to the activation of the dispenser, the amount of energy created and, if a contaminant sensor is provided, the reading of the contaminant sensor. Such data can be stored within the individual dispenser 10. Depending upon the amount of energy which may be stored at any given time and the power of storage for the dispenser of FIG. 16, the control nodule 52 of that dispenser 10 can then determine how frequently the stored information is to be relayed to the message collector. The amount of energy required for communication between the individual dispenser 10 and the message collector 310 including two-way communication to initialize and ensure there is proper communication generally is a greater amount of energy than that required for mere sensing and storage of information in the collecting dispenser 10. The frequency with which information may be transferred from the collecting dispenser to the message collector is preferably controlled by the controller in the collecting dispenser 10 is as to be a function of the amount of energy at any time within the power storage device in the collecting dispenser. For example, if the power storage device has energy above a first level, the information transferral may be every five minutes or, for example, every fifteen activations. If the power level in the storage device is below a given level, then the information transferral may be less frequent as, for example, every one, two, six or twelve hours. Information transfer would, for example, not be permitted to occur when the power level may fall below any particularly low limit. Thus, in accordance with the present invention, there is provided an improved arrangement for optimizing power consumption between a collecting dispenser and a message collector in which the frequency of communication of data from the collecting dispenser to the message dispenser is varied as a function of the power contained within a rechargeable power source in the collecting dispenser so as to reduce the frequency of information transferral as the power level decreases. This arrangement is useful whether or not a contaminant sensor 50 is provided on any dispenser.

The message collector 310 preferably is a dispenser which has with high probability an adequate availability of electrical power in its power storage device. Thus in an arrangement where a plurality of gathering dispensers 10 or other devices are provided for communicating their information to a message collector 310, the message collector 310 preferably has an increased and preferably continuous availability of power as, for example, by providing the message collector 310 to be hardwired to an A/C power system or, to have adequate replaceable batteries or, more preferably, to have a constant supply of renewable power. The constant supply of renewable power may be provided as by a solar panel, that is, a charging device which creates electrical energy from light and could, for example, have adequate capacity to provide power needs to the message controller for constant 24 hour operation based on the light it may receive. Another preferred element for use as the message collector is a fluid dispenser which incorporates an electrochemical cell to produce electric energy by chemical conversion of the fluid to be dispensed of the type disclosed, for example, in U.S. Pat. No. 7,530,477 to Ophardt, issued May 12, 2009, the disclosure of which is incorporated herein by reference. In FIG. 23, the message collector 310 preferably is such a combination fluid dispenser and electrochemical cell as disclosed in U.S. Pat. No. 7,530,477. With such a dispenser as the message collector 310, the fuel cell within the dispenser can produce electrical energy with time almost continuously and, in any event, periodically in amounts sufficient to provide energy for the constant operation of the message collector to monitor for incoming data from the plurality of other dispensers and devices which are attempting to communicate periodically via the WLAN 302 wirelessly. That is, in the message connector 310 dispenser which incorporates an electrochemical cell to produce electrical energy, the fluid which is to be dispensed for use as for cleaning hands, is also used as a source for electrochemical energy as by containing alcohol compounds that can in a fuel cell be converted to electrical energy for storage in a power storage device in the message collector dispenser. Thus, in a collage of elements such as illustrated in FIG. 22, one of the dispensers 10 may comprise a combination liquid dispenser and electrochemical cell which may serve as the message collector 310 and provide renewable energy during the time that its reservoir contains fluid to be dispensed. In accordance with the present invention, there is provided a novel arrangement comprising an array of fluid dispensers and other devices which collect and gather data and which communicate wirelessly periodically over short distances with the message collector which has enhanced power generation capability and is adapted for communication with other elements within a data distribution network such as to the internet 304 and facility manager 312 as seen in FIG. 22. Such arrangement is useful whether or not any contaminant sensors are included.

As seen in FIG. 16, the dispenser of the second embodiment has UBS port on its control module by which it may be connected with devices such as a computer of a facility manager 312 for configuration of the dispenser as may be desired, for example, initially or subsequently. After initial configuration, the dispenser 10 may preferably have the capability for being configured wirelessly and remotely. The control module 52 of the dispenser 10, particularly when it is a gathering dispenser with minimal power generation and storage capability preferably performs but minimalistic processing and its control module 52 may preferably be adapted for configuration wirelessly from time to time as may be desired by the facility manager 312. Similarly, the message collector 310 preferably is another dispenser 10 which may also be adapted for reconfiguration as by downloading of software from time to time preferably wirelessly as by the facility manager 312.

In FIG. 23, a portable wireless communication device such as a personal digital assistant or a smart phone 320 is illustrated as wireless communicating with the facility manager 312, the message collector 310 and the Internet 304. Such a smart phone 320 or other portable device may be carried by personnel for facility to permit timely transfer of matter about any particular of the sensing elements. In an arrangement more simplified than that illustrated in FIG. 23, the message collector 312 could communicate merely with the phone 320 and provide in a relatively smaller facility having, for example, possibly ten or twenty sensing elements a simplified arrangement for a person having the phone 320 as an intelligent portable communication device to be able to readily monitor activity of a number of dispensers 10 or other elements. In FIG. 22, each of the dispensers, including the liquid dispenser 10 and paper towel dispensers 202 may be provided with means of generating power as, for example, by having a power generator coupled to a manually activated lever which needs to be moved to dispense fluid. Other of the elements in the collage could similarly be provided to have power generators. For example, the door handle 229 could have an internal generator and thus be self powered such as in the manner of that disclosed in U.S. Patent Publication US 2010/0140499 to Casale, published on Jun. 10, 2010. On movement of the door handle 229 to open the door, the movement of the door handle 229 is translated by a generator to create power and this power can be used to power the wireless sensor 50 on the door.

The manner in which the data gathered from contaminant sensors is used, monitored and manipulated by the facility manager and the data processing unit is not limited. As discussed earlier in this application, thresholds may be established as to contamination levels for various contaminants which can be used to generate warnings and the like. However, there is no need to compare any data to thresholds. Data provided from the system can provide to the facility manager a record with time as to different contaminant levels at different locations in a facility. Those contaminant levels may be grouped as by time or by areas of the facility and the like. The contaminant levels provide the facility manager with a real time indication of matters which are being sensed. It is within the skill of persons skilled in the art to develop monitoring techniques to review trends and changes in the data towards identifying where difficulties and problems may arise. Such changes may be used towards providing early warnings of problems or possible problems. As but one example, if there might be an outbreak of a particular bacterial disease at a home for elderly people proximate to a hospital, the hospital may track the admission and presence of persons from that old age home in the hospital with a view to monitoring changes in levels of specific contaminants within specific areas of the hospital as an indication that contaminants may have been brought in with the persons from the old age home and counter-measure steps may be taken. In another example, outbreaks of influenza can be tracked on various Internet databases monitoring various factors from the population as a whole such as drug purchases, absenteeism and the like. Such data can be combined with data gathered from the sensors at a facility towards increased monitoring for particular contaminants or to reacting more quickly upon changes in the levels of certain specific contaminants sensed.

The present invention provides a community of sensors and can use group behaviour strategies to identify various signals and device malfunction. A wide array of dispensers and other elements carrying sensors provides a widely distributed sensor network.

In accordance with the present invention, there is provided a method of large scale bio-sensing using the preferred sensor carrying dispensers and other sensor carrying elements in accordance with the present invention. In accordance with the present invention, three factors are of particular usefulness, these factors being the time of insertion of a replaceable bottle or cartridge in a dispenser, the usage by people of that dispenser with time and the level of a biologic contaminant on the sensor at the dispenser with time as, for example, giving a bacterial count. The three factors represented over time of the insertion of a reservoir, the usage of a dispenser and the bacterial levels on a dispenser with time provide a foundation towards determining the hygienic status of any health care facility. The particular nature of the data gathered from a large array of dispensers and other sensing elements within a facility is provided in conjunction with a network framework for collecting, filtering and processing large volumes of real time data. Data is provided from a large number of data sources providing the live network data. This mining of rich real time data provides a system which can be used to understand the network's operation and, as well, to detect anomalies in the data and the like.

As one means of communication of a signal from a sensor 50, a RFID system may be used comprising a Radio Frequency Identification (RFID) device in combination with an RFID reader to pass on a signal as to facility operators. The RFID device can be active, passive or a hybrid thereof A passive RFID device includes an antenna to capture sufficient energy from a surrounding electromagnetic field to power the RFID device. The antenna is electrically connected to an electronic chip which performs the various pre-programmed RFID functions. An RFID reader used in conjunction with passive RFID devices generates an electromagnetic field of sufficient intensity or magnetic flux to power the RFID device 20 when the RFID device is proximal to a reader. For example, known RFID readers 30 can produce a field such that a RFID device located can be energized and interrogated by the RFID reader at distances of up to at least ten feet. An active RFID device includes an energy source such as an embedded battery for the energy to transmit signals to the RFID reader. Hybrid RFID devices have characteristics of both passive and active devices inasmuch as such devices capture energy from a surrounding electromagnetic field but also employ a battery improve range of communication.

Figure 24:
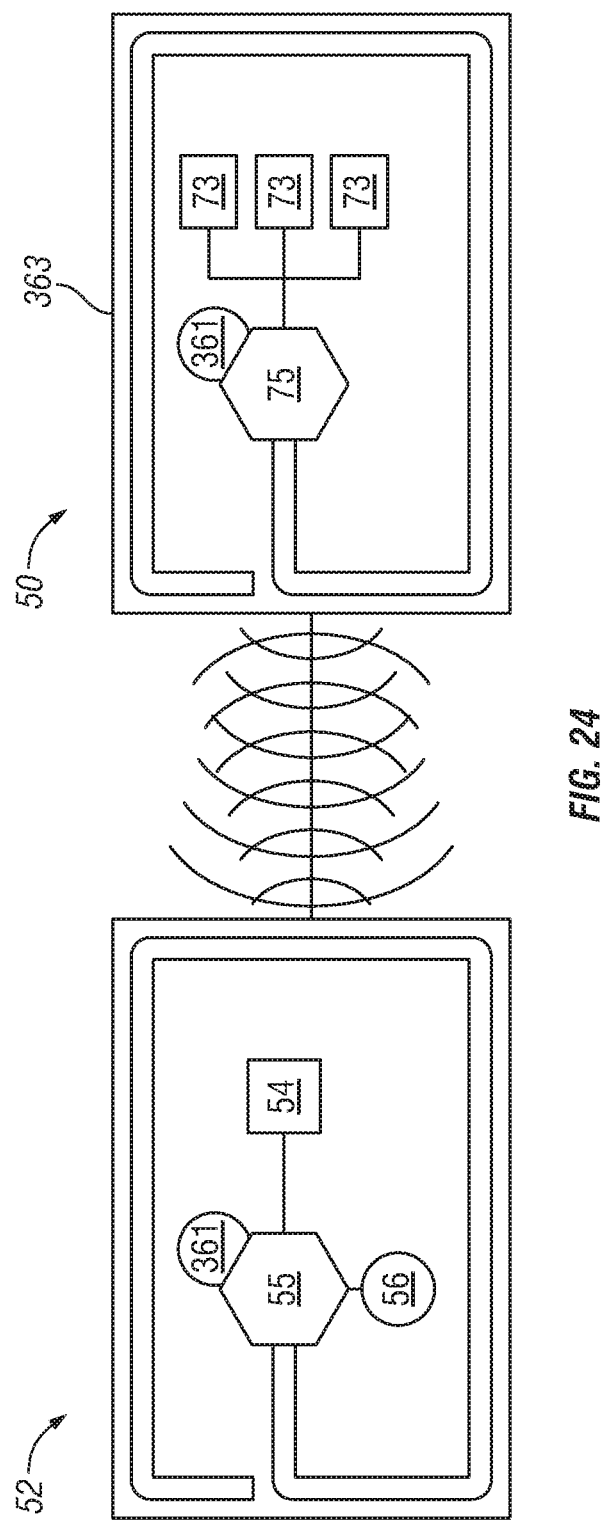
FIG. 24 is a schematic representation of use of an RFID system for communication of signals from one or more sensors.

Reference is made to FIG. 24 which shows a sensor arrangement comprising a wireless sensor 50 and a control unit 52 similar to that shown in FIG. 9 but using RFID technology. The sensor 50 includes as at least part of its processor 75 a RFID transponder 361. A RFID reader or transceiver 362 is provided as part of the control unit 52. On the sensor 50, the processor 75 and its RFID transponder 361 are shown connected to a plurality of different contaminant sensing mechanisms 73 and to an antenna 259. The wireless sensor 50 is preferably is manufactured as by printing its various elements onto a flexible substrate 363. Selecting the RFID transponder to be a passive RFID transponder without a battery assists in ease of manufacture. Preferably, each of the processor 75, the antenna 78 and the sensor processor 75 may be printed directly onto a flexible substrate as by inkjet printing techniques, however, if this is not possible for any one of the components then, for example, one or more of the components such as the sensing mechanism 73 and sensor processor 75 may be manufactured by another process and integrated onto the flexible substrate 363. The substrate may preferably comprise a flexible substrate such as polymers of PET, PEN and PI and on flexible foils and laminates.

In the context of FIGS. 22 and 23, the RFID wireless sensor 50 of FIG. 24 may be provided as the sensor on any one of the elements in FIG. 22 such as the handrail and the toilet handle, and the control unit 52 may be provided for example on the message collector 310, For each dispenser 10 the RFID wireless sensor 50 may be provided on a removable reservoir and the control unit 52 on the dispenser housing. The RFID transceiver or reader can be adapted to communicate with various devices including a processor in the dispenser, another dispenser which acts as a message collector, a router, the Internet or correctly with the facility manager.

As an example of a type of biosensor which could be adapted for use as one or more of the sensors 50 in accordance with the present invention is the biosensor disclosed in U.S. Pat. No. 7,651,843 to Stubbs et al, issued Jan. 26, 2010, the disclosure of which is incorporated herein by reference. Stubbs discloses an acoustical wave biosensor adapted to identify bacteria, micro-organisms or plants in a liquid or gaseous medium in which the bacteria, micro-organisms or plants are of a kind which produce signalling molecules in a vapour space or liquid about the subject species within an environment. Stubbs teaches an acoustical wave biosensor positioned to sense vapour for the signalling chemical within gas in the environment or sense the signalling chemical within a liquid forming the environment and in each case to perform a real time evaluation of the presence of the signalling chemicals. The above-noted patent to Stubbs teaches the use of an acoustical wave biosensor useful for determining the presence of bacteria in real time from gas or liquid medium and teaches, for example, real time detection of *Bacillus* related species including, for example, air borne micro-organisms such as *Bacillus subtilis*. The acoustical wave biosensor may be an RFID type sensor as described in U.S. Pat. No. 7,053,524 to Edmonson et al, issued May 30, 2006, the disclosure of which is incorporated herein by reference.

The nature of the wireless sensor for use with the present invention is not limited. However toward providing low cost sensors, the use of relatively inexpensive plastic or foil substrates and low cost printing methods are preferred manners of manufacture.

Figure 25:
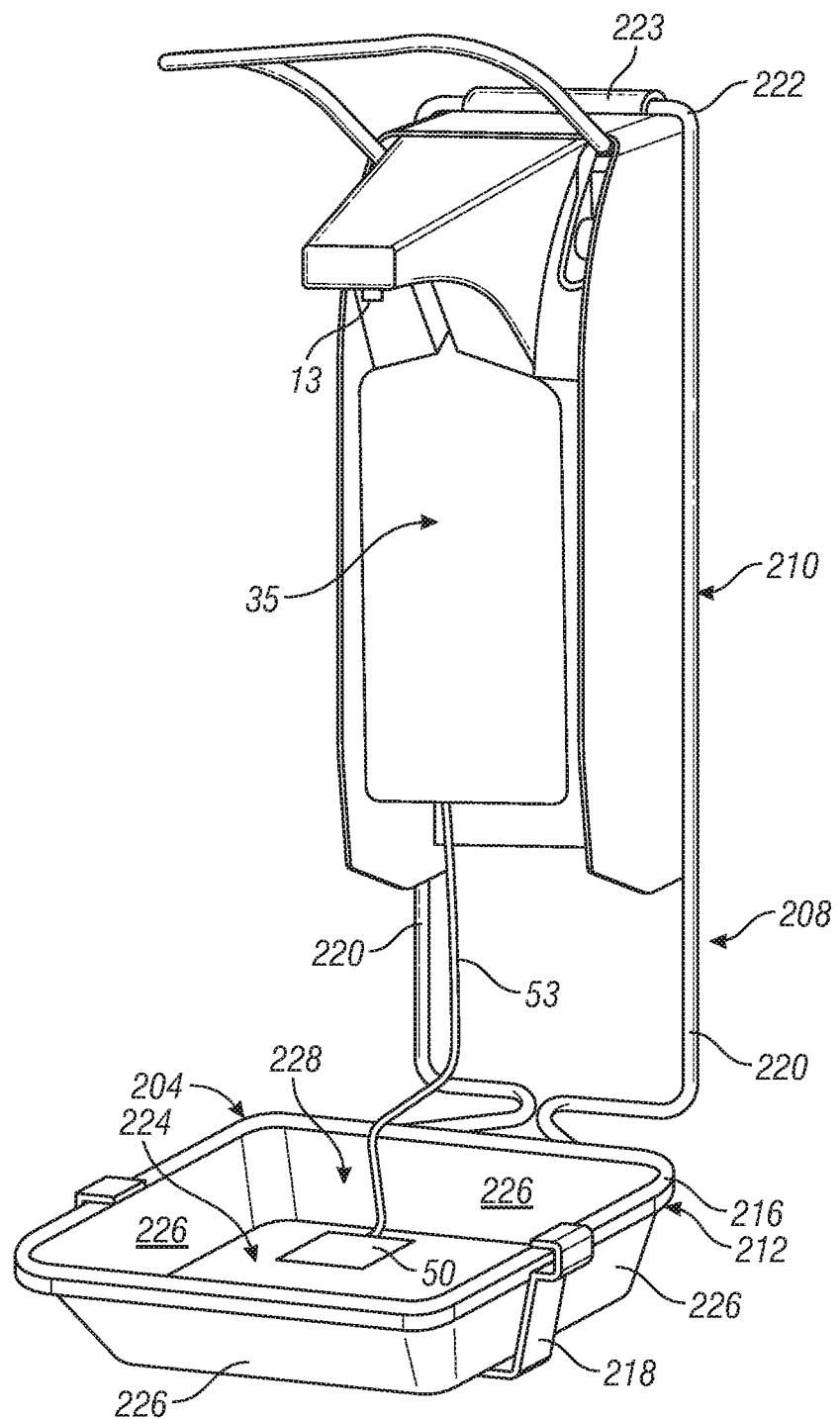
FIG. 25 is a front perspective view of a soap dispenser in accordance with a fifth embodiment of the invention including a drip tray.
Figure 26:
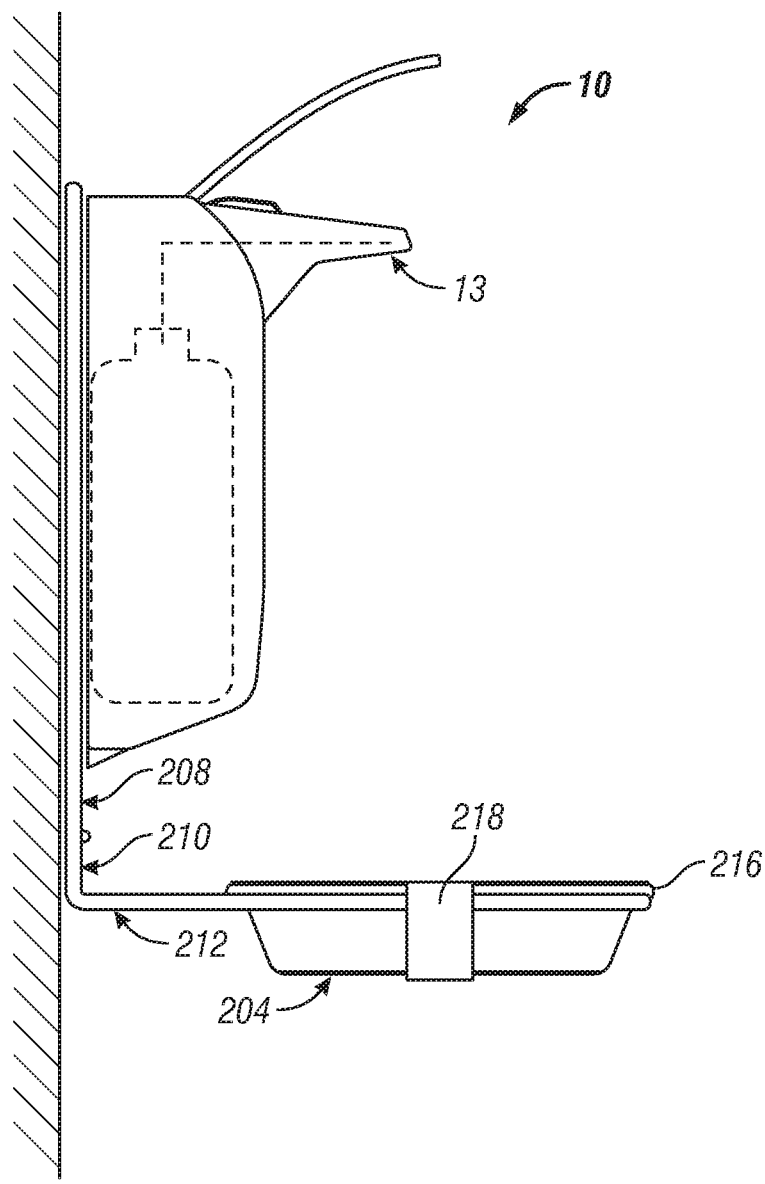
FIG. 26 is a side view of the dispenser of FIG. 25.
Figure 27:
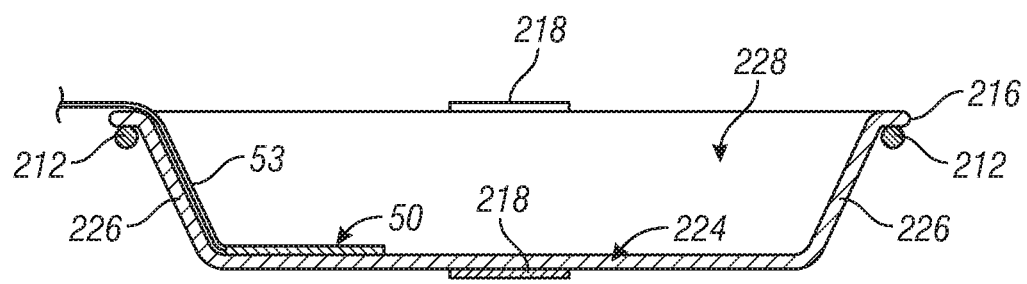
FIG. 27 is a vertical cross-sectional side view through the drip tray shown in FIGS. 25 and 26.

Reference is made to FIGS. 25, 26 and 27 which illustrate a fifth embodiment of a dispenser in accordance with the present invention in which the dispenser 10 is identical to that disclosed in the first embodiment of FIGS. 1 to 6 with the exceptions of, firstly, the inclusion of a dip tray 204 provided below the dispenser outlet nozzle 13 and with the contaminant sensor 50 carried by the drip tray 204. As shown, the dip tray 204 is removably supported vertically below the nozzle 13. In use, fluid is dispensed onto a user's hand below the nozzle 13 and fluid may drip from the user's hand downwardly. The drip tray 204 is provided to catch such dripping fluid and prevent it from dripping onto the floor or a countertop or other surface underneath the dispenser 10. Oftentimes, a user will, after dispensing fluid onto one hand disposed below the nozzle 13, then rub the user's hands together below the nozzle 11 above the drip tray 204 such that fluid dripping from the hands during dispensing and rubbing is caught in the drip tray 204. Such drip trays 204 are particularly useful when the fluid is sprayed as by a spray nozzle or missed from the nozzle 13 and where the fluid is a low viscosity fluid such as alcohol which can readily drip from a user's hand.

The drip tray 204 is shown as supported from the dispenser 10 via a rigid support 208 formed from a rigid metal rod and having, as seen in FIG. 26, a vertically disposed rear loop 210 fixedly supporting a horizontally disposed horizontal loop 212. The horizontal loop 212 provides an opening sized to receive the drip tray 204 therein with an outwardly extending lip 216 of the drip tray 204 extending outwardly over the rod of the horizontal loop 214. A spring clip member 218 extends from above the lip 216 of the drip tray 204 on one side under the tray to the other side to securely bias the drip tray 204 downwardly into the loop 212. The spring clip member 218 is horizontally slidable relative to the drip tray 204 and the horizontal loop 212 to permit removal of the drip tray from the horizontal loop 212 as, for example, for cleaning or disposal of any fluid caught by the drip tray.

Figure 28:
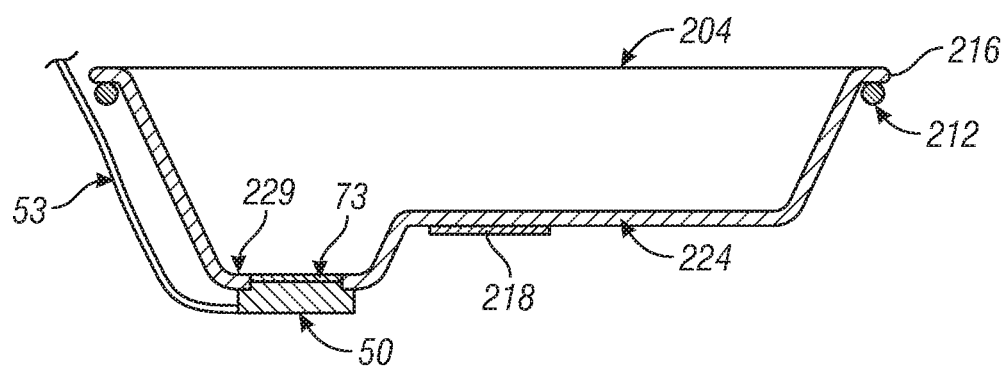
FIGS. 28, 29 and 30 is each a cross-sectional side view the same as FIG. 27, however, showing a different configuration for the contaminant sensor.

The vertical loop 212 has side members 220 that extend upwardly on either side of the dispenser 10 and are joined by a horizontal top member 222 coupled to the dispenser 10, preferably to the upper rear of a wall plate 223 for the dispenser 10 for pivoting about a horizontal axis through the top member 222 as can be of assistance to insert and remove the removable bottle 35. The drip tray has a bottom 224 from which side walls 226 extend upwardly to form an internal well 228 to catch fluid. The contaminant sensor 50 is carried on the drip tray 212 so as to be in communication with fluid from the well 228. As seen in FIGS. 26 and 28, the sensor 50 is provided secured to the drip tray 204 in the well 228 to the upper surface of the bottom 224 at a location that under gravity fluid in the drip tray 204 will come into engagement with the sensor 50. Wires 53 are shown to extend from the sensor 50 to couple the sensor 50 as to a control module (not shown) similar to the control modular 52 and in a similar manner to that shown in the first embodiment of FIGS. 1 to 6. The sensor 50 may have other configurations as illustrated, for example, in FIG. 9 or as described and shown with other of the embodiments.

The sensor 50 carried by the drip tray 204 can sense contaminants in the fluid in the drip tray and thus provide an indication of contaminants which may have originated as on a person's hand using the drip tray or otherwise as, for example, on the nozzle 13 or which have come to be in the fluid as by environmental air coming to engage fluid within the drip tray. The particular nature of the sensor 50 carried by the drip tray 204 is not limited, however, preferably, is a sensor 50 which is adapted for sensing contaminants within a liquid.

Reference is made to FIG. 28 which shows a cross-section through the drip tray similar to that shown in FIG. 27, however, with the sensor 50 shown as having a contaminant sensing mechanism 73 disposed at a low point in a lower sump 229 of the well 228 of the drip tray 204 such that any fluid in the drip tray 204 will necessarily be in communication with the contaminant sensing mechanism 73 of the sensor 50. In the embodiment of FIG. 28, the sensor 50 is illustrated as being sealably engaged within an opening through the bottom 224 of the drip tray 204 under the sump 229 and thus can, for example, provide other components of the sensor 50 outside of the well 228 of the drip tray 204 and including the wires 53.

Figure 29:
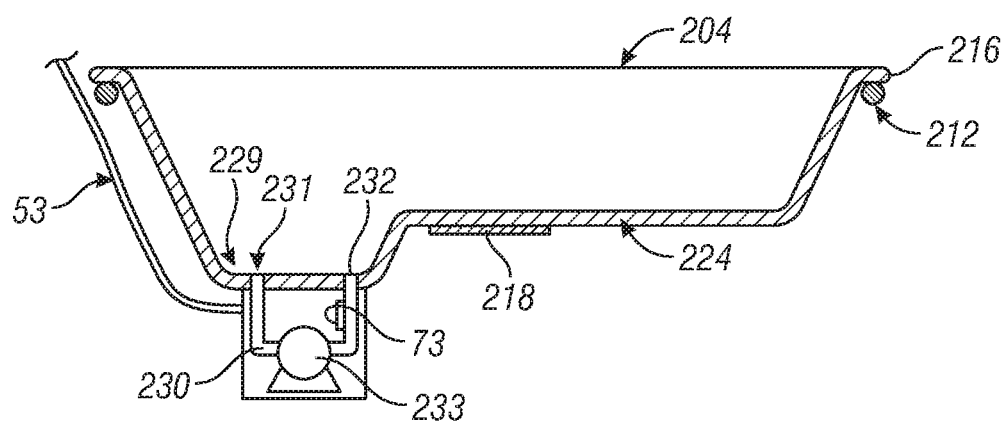

Reference is made to FIG. 29 which illustrates another cross-section through the drip tray similar to that shown in FIG. 28, however, showing an alternate arrangement of a sensor 50 in which the sensor 50 is schematically illustrated as including a passageway 230 in communication with the fluid in the well 228 via an inlet 231 and an outlet 232. The sensor 50 is indicated as including a pump 233 to draw fluid from the well via the inlet and discharge it by the outlet. A contaminant sensing mechanism 73 is schematically illustrated as being provided at a location along the passageway 230 such that the sensor 50 effectively senses contaminants in the fluid drawn through the sensor 50. It is to be appreciated that the pump may have an extremely low rate of volumetric flow and may be operated merely periodically.

Figure 30:
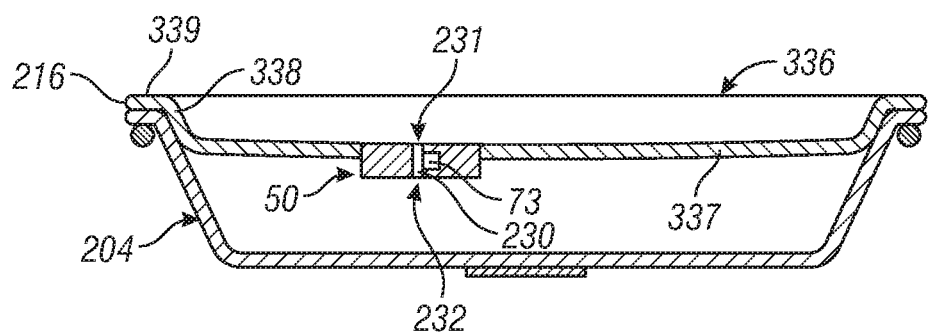

Reference is made to FIG. 30 which illustrates another cross-sectional view through the drip tray similar to FIG. 27, however, showing a catch tray 336 nestled over the trip tray 204 to overlie the trip tray 204. The catch tray 336 has a bottom 337 and sides 338 which extend up to a lip 339 which overlies the lip 216 of the trip tray 204. The sensor 50 is sealed in an opening through the bottom 337 of the catch tray 336. The sensor 50 has a passageway 230 therethrough with an inlet 231 open to the catch tray 336 and an outlet 232 which opens downwardly into the drip tray 204. Fluid within the catch tray 336 under gravity will pass through the passageway 230 of the sensor 50 and into the catch basin. Fluid passing through the passageway 230 comes into contact with the sensing mechanism 73 so as to sense contaminants in the fluid.

Figure 31:
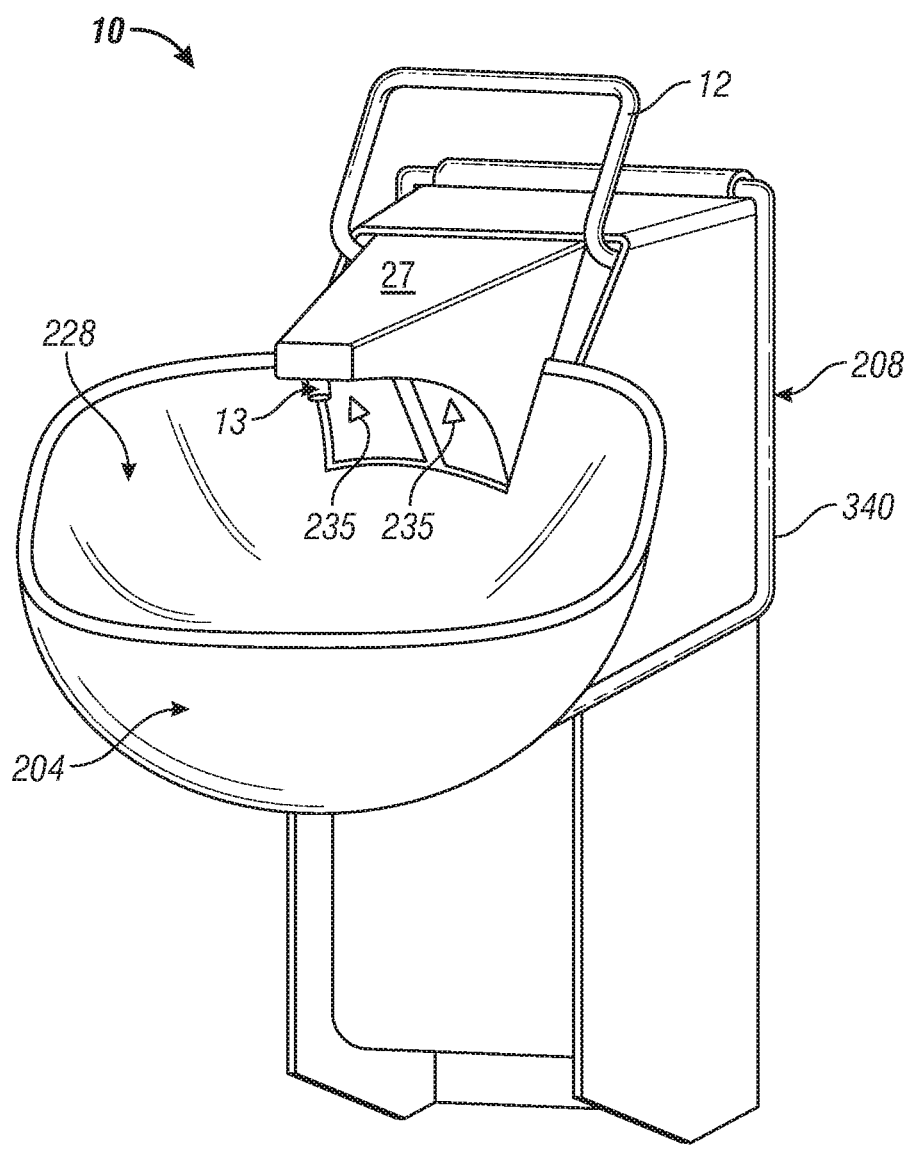
FIG. 31 is a front perspective view of a soap dispenser in accordance with a sixth embodiment of the invention including a drip tray.

Reference is made to FIG. 31 which illustrates a sixth embodiment of a dispenser in accordance with the present invention which comprises a touchless dispenser 10 including a drip tray 204. The dispenser 10 shown in FIG. 31 is a touchless version of a dispenser of the type shown in FIG. 1 in which hand sensors 235 are provided under the nozzle shield 27 and adapted to activate an electric motor (not shown) to move a piston pump (not shown) to dispense fluid out the nozzle 13 onto a user's hand. As contrasted with the embodiment of FIG. 26, in FIG. 31, the drip tray 204 is located in closer proximity to the nozzle 13 underneath the nozzle 13 and provides a bowl-like containment well 228 supported on a rigid support 208 from the dispenser. The drip tray 204 thus provides a bowl-like well 228 of a diameter and depth to permit a user to locate a user's hand underneath the nozzle 13 above the drip tray 204 possibly at least partially within the well 228 with sufficient room for both hands to receive fluid underneath the nozzle 13 and be rubbed together underneath the nozzle 13 and above or within the drip tray 204 such that substantially all errant spray from the nozzle 13 or dripping from a user's hands may be captured by the drip tray 204. The dispenser 10 is shown includes a lever 12 adapted to be manually moved by a user to dispense fluid from the nozzle if the electric motor is not powered or not working. The drip tray 214 is supported by the rigid support member 208 which includes L-shaped side members 340 which extend from underneath the drip tray 204 rearwardly along the sides of the dispenser 10 then upwardly to a top member which extends across the top of the dispenser 10.

In FIGS. 28 to 30, embodiments of the contaminant sensor 50 are shown which are not merely thin sheet members and in which provision is made for movement of a liquid past the contaminant sensing mechanism 73 of the sensor 50. Dispensers with sensors which are to sense airborne contaminants can similarly be provided with various mechanisms to provide for movement of air from the environment about a dispenser into contact with the contaminant sensing mechanism.

While the invention has been described with reference to preferred embodiments, many modifications and variations will now occur to persons skilled in the art. For a definition of the invention, reference is made to the appended claims.

I claim:

1. A method of operating a fluid dispenser for dispensing fluid for cleaning a person's hands comprising:
    discharging as a discharged fluid a hand cleaning fluid from a discharge outlet,
    providing a drip tray located below the discharge outlet,
    providing a space below the discharge outlet and vertically above the drip tray within which one hand or both hands of the person can be placed to have fluid dispensed from the discharge outlet engage the one hand or both hands,
    providing a person's hand below the discharge outlet in the space,
    providing a sensor carried by the dispenser,
    discharging the discharged fluid from the discharge outlet into engagement with the person's hand,
    dripping part of the discharged fluid in engagement with the person's hand into the drip tray,
    capturing a portion of the discharged fluid in the drip tray wherein the portion of the discharged fluid captured in the drip tray includes dispensed fluid that has been engaged with the person's hand and dripped into the drip tray, and
    passing the portion of the discharged fluid to the sensor, and detecting with the sensor a relative level of a contaminant in the portion of the discharged fluid.

2. A method as claimed in claim 1 including: after the discharged fluid has been discharged into engagement with the person's hand, rubbing the user's hands together within the space.

3. A method as claimed in claim 1 wherein the contaminant comprising a biologic pathogen or a product of the biologic pathogen.

4. A method as claimed in claim 1 including signaling the presence of the contaminant.

5. A method as claimed in claim 1 including:
    capturing the portion of the discharged fluid in the drip tray by permitting the portion of the discharged fluid to flow under gravity in the drip tray into a well in the drip tray,
    providing the sensor in the well at a location where the portion that flows under gravity in the drip tray into the well engages the sensor.

6. A method as claimed in claim 1 including: capturing the portion of the discharged fluid in the drip tray by permitting the discharged fluid to flow under gravity in the drip tray into a well in the drip tray, providing a passageway having an inlet in communication with the discharged fluid in the well and an outlet, and with the sensor at a location along the passageway, passing the portion of the discharged fluid through the passageway from the inlet to the outlet to pass the fluid past the sensor.

7. A method as claimed in claim 6 including utilizing a pump to pass the portion of the discharged fluid through the passageway.

8. A method as claimed in claim 6 wherein the contaminant comprising a biologic pathogen or a product of the biologic pathogen.

9. A fluid dispenser for dispensing fluid for cleaning a person's hands,
    the dispenser comprising: (a) a fluid containing reservoir, (b) a first pump to dispense fluid from the reservoir out a discharge outlet, (c) a drip tray located below the discharge outlet to catch fluid dispensed from the dispenser, and (d) a sensor mechanism,
    the sensor mechanism comprising a passageway with an inlet and an outlet, and a sensor at a location along the passageway, the sensor operative to detect a relative level of a contaminant, the inlet of the passageway in communication with the fluid caught in the drip tray, the sensor sensing contaminants in the fluid passed through the passageway,
    the drip tray is located below the discharge outlet providing a space below the discharge outlet and vertically above the drip tray within which one hand or both hands of the person are placed to have fluid dispensed from the discharge outlet engage the one or both of the hands, the drip tray configured to catch fluid dispensed from the discharge outlet that drips from the one or both of the hands when the one or both of the hands are in the space, the inlet is in communication with the drip tray at a location in the drip tray where fluid that is caught by the drip tray will flow under gravity to the inlet.

10. A fluid dispenser as claimed in claim 9 wherein the contaminant comprising a biologic pathogen or a product of the biologic pathogen signaling the presence of the pathogen.

11. A fluid dispenser as claimed in claim 9 further including: e) a second pump passing fluid caught in the drip tray through the passageway past the sensor.

12. A fluid dispenser as claimed in claim 9 wherein the passageway providing for fluid in the inlet to flow under gravity through the passageway past the sensor to the outlet.

13. A fluid dispenser as claimed in claim 9, wherein the drip tray has a bottom and side walls forming an upwardly open internal well to catch fluid, the well having a lower sump within which fluid caught by the drip tray will flow under gravity, the inlet provided in the sump.

14. A fluid dispenser as claimed in claim 9 wherein the drip tray is located below the discharge outlet to catch fluid discharged from the discharge outlet or dripping from the discharge outlet when the one or both of the hands are not within the space.

15. A fluid dispenser as claimed in claim 10 including: (f) a signal generator for generating a signal representative of the level of the contaminant on the sensor.

16. A fluid dispenser as claimed in claim 14 further including: (g) a second pump passing fluid caught in the drip tray through the passageway past the sensor, and wherein the contaminant comprising a biologic pathogen or a product of the biologic pathogen signaling the presence of the pathogen.

17. A fluid dispenser as claimed in claim 14 wherein the space is a space within which the hands can be rubbed together.

18. A fluid dispenser as claimed in claim 14 wherein the contaminant comprising a biologic pathogen or a product of the biologic pathogen signaling the presence of the pathogen.

19. A method as claimed in claim 1 including providing the sensor in the drip tray.

20. A method as claimed in claim 1 wherein the drip tray feeds the portion to the sensor.

21. A method as claimed in claim 5 wherein the portion flows under gravity from the inlet to the outlet through the passageway past the sensor.

22. A method of operating a fluid dispenser for dispensing fluid for cleaning a person's hands comprising:

discharging as a discharged fluid a hand cleaning fluid from a discharge outlet,
providing a drip tray located below the discharge outlet,
providing a space below the discharge outlet and vertically above the drip tray within which one hand or both hands of the person can be placed to have fluid dispensed from the discharge outlet engage the one hand or both hands,
providing a person's hand below the discharge outlet in the space,
discharging the discharged fluid from the discharge outlet into engagement with the person's hand,
dripping art of the discharged fluid in engagement with the person's hand into the drip tray,
capturing a portion of the discharged fluid in the drip tray wherein the portion of the discharged fluid captured in the drip tray includes dispensed fluid that has been engaged with the person's hand and dripped into the drip tray, and
detecting with the sensor a relative level of a contaminant in the portion of the discharged fluid.

23. A method of operating a fluid dispenser for dispensing fluid for cleaning a person's hands,
wherein the fluid dispenser includes a discharge outlet, a drip tray located below the discharged outlet, a space below the discharge outlet and vertically above the drip tray within which one hand or both hands of the person can be placed to have fluid dispensed from the discharge outlet engage the one hand or both hands, and a sensor,
the method comprising: discharging as a discharged fluid a hand cleaning fluid from the discharge outlet,
providing a person's hand below the discharge outlet in the space, discharging the discharged fluid from the discharge outlet into engagement with the person's hand,
dripping part of the discharged fluid in engagement with the person's hand into the drip tray,
capturing a portion of the discharged fluid in the drip tray wherein the portion of the discharged fluid captured in the drip tray includes dispensed fluid that has been engaged with the person's hand and dripped into the drip tray, and
detecting with a sensor a relative level of a contaminant in the portion of the discharged fluid.

24. A method as claimed in claim 2 including passing the portion of the discharged fluid to the sensor.

\* \* \* \* \*